United States Patent
Darvish et al.

(10) Patent No.: US 8,346,363 B2
(45) Date of Patent: Jan. 1, 2013

(54) BLOOD GLUCOSE LEVEL CONTROL

(75) Inventors: Nissim Darvish, Hof-Hacarmel (IL); Tami Harel, Haifa (IL); Bella Felsen, Haifa (IL)

(73) Assignee: MetaCure Limited, Hamilton (BM)

( * ) Notice: Subject to any disclaimer, the term of this patent is extended or adjusted under 35 U.S.C. 154(b) by 579 days.

(21) Appl. No.: 11/318,845

(22) Filed: Dec. 27, 2005

(65) Prior Publication Data

US 2006/0184207 A1    Aug. 17, 2006

Related U.S. Application Data

(62) Division of application No. 09/914,889, filed as application No. PCT/IL00/00132 on Mar. 5, 2000, now Pat. No. 7,006,871.

(60) Provisional application No. 60/123,532, filed on Mar. 5, 1999.

(51) Int. Cl.
*A61N 1/00* (2006.01)
(52) U.S. Cl. ............................................. 607/40; 607/22
(58) Field of Classification Search ................... 607/22, 607/40
See application file for complete search history.

(56) References Cited

U.S. PATENT DOCUMENTS

| | | |
|---|---|---|
| 1,918,386 A | 7/1933 | Esau |
| 3,541,390 A | 11/1970 | Jahnke |
| 3,572,345 A | 3/1971 | Auphan |
| 3,587,567 A | 6/1971 | Schiff |
| 3,651,805 A | 3/1972 | Breiling |
| 3,651,806 A | 3/1972 | Hirshberg |
| 3,911,930 A | 10/1975 | Hagfors et al. |
| 3,924,641 A * | 12/1975 | Weiss ................................ 607/74 |
| 3,933,147 A | 1/1976 | Du Vall et al. |
| 3,942,536 A | 3/1976 | Mirowski et al. |
| 3,944,740 A | 3/1976 | Murase et al. |
| 3,952,750 A | 4/1976 | Mirowski et al. |
| 4,030,509 A | 6/1977 | Heilman et al. |
| 4,055,190 A * | 10/1977 | Tany ................................... 607/46 |
| 4,106,494 A | 8/1978 | McEachern |
| 4,164,216 A | 8/1979 | Person |
| 4,168,711 A | 9/1979 | Cannon, III et al. |
| 4,184,493 A | 1/1980 | Langer et al. |
| 4,202,340 A | 5/1980 | Langer et al. |
| 4,223,678 A | 9/1980 | Langer et al. |
| 4,237,895 A | 12/1980 | Johnson |
| 4,273,114 A | 6/1981 | Barkalow et al. |

(Continued)

FOREIGN PATENT DOCUMENTS

EP        0148687        7/1985

(Continued)

OTHER PUBLICATIONS

Notice of Allowance Dated Dec. 28, 2010 From the US Patent and Trademark Office Re.: U.S. Appl. No. 11/932,064.

(Continued)

*Primary Examiner* — Nicole F Lavert

(57) ABSTRACT

A pancreatic controller, comprising:
  a glucose sensor, for sensing a level of glucose or insulin in a body serum;
  at least one electrode, for electrifying an insulin producing cell or group of cells;
  a power source for electrifying said electrode with a pulse that does not initiate an action potential in said cell and has an effect of increasing insulin secretion; and
  a controller which receives the sensed level and controls said power source to electrify said electrode to have a desired effect on said level.

47 Claims, 7 Drawing Sheets

U.S. PATENT DOCUMENTS

| | | | |
|---|---|---|---|
| 4,293,734 A | 10/1981 | Pepper, Jr. | |
| 4,312,354 A | 1/1982 | Walters | |
| 4,316,472 A | 2/1982 | Mirowski et al. | |
| 4,337,776 A | 7/1982 | Daly et al. | |
| 4,384,585 A | 5/1983 | Zipes | |
| 4,387,717 A | 6/1983 | Brownlee et al. | |
| 4,403,614 A | 9/1983 | Engle et al. | |
| 4,406,288 A | 9/1983 | Horwinski et al. | |
| 4,407,288 A | 10/1983 | Langer et al. | |
| 4,411,268 A | 10/1983 | Cox | |
| 4,428,366 A | 1/1984 | Findl et al. | |
| 4,440,172 A | 4/1984 | Langer | |
| 4,506,680 A | 3/1985 | Stokes | |
| 4,537,195 A | 8/1985 | McDonnell | |
| 4,537,203 A | 8/1985 | Machida | |
| 4,543,738 A | 10/1985 | Mower | |
| 4,543,956 A | 10/1985 | Herscovici | |
| 4,550,221 A | 10/1985 | Mabusth | |
| 4,554,922 A | 11/1985 | Prystowsky et al. | |
| 4,559,946 A | 12/1985 | Mower | |
| 4,566,456 A | 1/1986 | Koning et al. | |
| 4,572,191 A | 2/1986 | Mirowski et al. | |
| 4,628,934 A | 12/1986 | Pohndorf et al. | |
| 4,639,720 A | 1/1987 | Rympalski et al. | |
| 4,651,716 A | 3/1987 | Forester et al. | |
| 4,674,508 A | 6/1987 | DeCote | |
| 4,679,572 A | 7/1987 | Baker, Jr. | |
| 4,686,332 A | 8/1987 | Greanias et al. | |
| 4,690,155 A | 9/1987 | Hess | |
| 4,726,279 A | 2/1988 | Kepler et al. | |
| 4,726,379 A | 2/1988 | Altman et al. | |
| 4,765,341 A | 8/1988 | Mower et al. | |
| 4,830,006 A | 5/1989 | Haluska et al. | |
| 4,834,100 A | 5/1989 | Charms | |
| 4,850,959 A | 7/1989 | Findl | |
| 4,870,974 A | 10/1989 | Wang | |
| 4,878,553 A | 11/1989 | Yamanami et al. | |
| 4,914,624 A | 4/1990 | Dunthorn et al. | |
| 4,928,688 A | 5/1990 | Mower | |
| 4,979,507 A | 12/1990 | Heinz et al. | |
| 4,988,837 A | 1/1991 | Murakami et al. | |
| 4,998,531 A | 3/1991 | Bocchi et al. | |
| 5,002,052 A | 3/1991 | Haluska et al. | |
| 5,003,976 A | 4/1991 | Alt | |
| 5,020,544 A | 6/1991 | Dahl et al. | |
| 5,022,396 A | 6/1991 | Watanabe | |
| 5,026,397 A | 6/1991 | Aoki et al. | |
| 5,031,617 A | 7/1991 | Klettner | |
| 5,044,375 A | 9/1991 | Bach, Jr. et al. | |
| 5,050,612 A | 9/1991 | Matsumura | |
| 5,083,564 A | 1/1992 | Scherlag | |
| 5,085,218 A | 2/1992 | Heil et al. | |
| 5,087,243 A | 2/1992 | Avitall | |
| 5,097,832 A | 3/1992 | Buchanan | |
| 5,097,833 A | 3/1992 | Campos | |
| 5,097,843 A | 3/1992 | Soukup et al. | |
| 5,111,815 A | 5/1992 | Mower | |
| 5,129,394 A | 7/1992 | Mehra | |
| 5,133,354 A | 7/1992 | Kallok | |
| 5,137,021 A | 8/1992 | Wayne et al. | |
| 5,144,554 A | 9/1992 | Zhang et al. | |
| 5,156,147 A | 10/1992 | Warren et al. | |
| 5,156,149 A | 10/1992 | Hudrlik | |
| 5,161,527 A | 11/1992 | Nappholz et al. | |
| 5,163,428 A | 11/1992 | Pless | |
| 5,172,690 A | 12/1992 | Nappholz et al. | |
| 5,174,286 A | 12/1992 | Chirife | |
| 5,188,106 A | 2/1993 | Nappholz et al. | |
| 5,190,036 A * | 3/1993 | Linder | 607/42 |
| 5,190,141 A | 3/1993 | Boldrini et al. | |
| 5,199,428 A | 4/1993 | Obel et al. | |
| 5,205,284 A | 4/1993 | Freeman | |
| 5,213,098 A | 5/1993 | Bennett et al. | |
| 5,231,381 A | 7/1993 | Duwaer | |
| 5,231,988 A * | 8/1993 | Wernicke et al. | 607/118 |
| 5,233,985 A | 8/1993 | Hudrlik | |
| 5,236,413 A | 8/1993 | Feiring | |
| 5,282,785 A | 2/1994 | Shapland et al. | |
| 5,284,491 A | 2/1994 | Sutton et al. | |
| 5,286,254 A | 2/1994 | Shapland et al. | |
| 5,292,344 A | 3/1994 | Douglas | |
| 5,305,745 A | 4/1994 | Zacouto | |
| 5,320,642 A | 6/1994 | Scheriag | |
| 5,320,643 A | 6/1994 | Roline et al. | |
| 5,324,327 A | 6/1994 | Cohen | |
| 5,327,887 A | 7/1994 | Nowakowski | |
| 5,346,506 A | 9/1994 | Mower et al. | |
| 5,350,403 A | 9/1994 | Stroetmann et al. | |
| 5,353,800 A | 10/1994 | Pohndorf et al. | |
| 5,365,461 A | 11/1994 | Stein et al. | |
| 5,366,486 A | 11/1994 | Zipes et al. | |
| 5,368,040 A | 11/1994 | Carney | |
| 5,370,665 A | 12/1994 | Hudrlik | |
| 5,381,160 A | 1/1995 | Landmeier | |
| 5,386,837 A | 2/1995 | Sterzer | |
| 5,387,419 A | 2/1995 | Levy et al. | |
| 5,391,192 A | 2/1995 | Lu et al. | |
| 5,391,199 A | 2/1995 | Ben-Haim | |
| 5,397,344 A | 3/1995 | Garfield et al. | |
| 5,398,683 A | 3/1995 | Edwards et al. | |
| 5,402,151 A | 3/1995 | Duwaer | |
| 5,411,531 A | 5/1995 | Hill et al. | |
| 5,415,629 A | 5/1995 | Henley | |
| 5,417,717 A | 5/1995 | Salo et al. | |
| 5,419,763 A | 5/1995 | Hildebrand | |
| 5,423,872 A | 6/1995 | Cigaina | |
| 5,425,363 A | 6/1995 | Wang | |
| 5,431,688 A | 7/1995 | Freeman | |
| 5,433,730 A | 7/1995 | Alt | |
| 5,443,485 A | 8/1995 | Housworth et al. | |
| 5,447,520 A | 9/1995 | Spano et al. | |
| 5,447,526 A | 9/1995 | Karsdon | |
| 5,458,568 A | 10/1995 | Racchini et al. | |
| 5,464,020 A | 11/1995 | Lerner | |
| 5,468,254 A | 11/1995 | Hahn et al. | |
| 5,472,453 A | 12/1995 | Alt | |
| 5,476,484 A | 12/1995 | Hedberg | |
| 5,476,485 A | 12/1995 | Weinberg et al. | |
| 5,476,497 A | 12/1995 | Mower et al. | |
| 5,482,052 A | 1/1996 | Lerner | |
| 5,499,971 A | 3/1996 | Shapland et al. | |
| 5,501,662 A | 3/1996 | Hofmann | |
| 5,510,813 A | 4/1996 | Makinwa et al. | |
| 5,514,162 A | 5/1996 | Bornzin et al. | |
| 5,520,642 A | 5/1996 | Bigagli et al. | |
| 5,528,002 A | 6/1996 | Katabami | |
| 5,531,764 A | 7/1996 | Adams et al. | |
| 5,540,722 A | 7/1996 | Clare et al. | |
| 5,540,730 A | 7/1996 | Terry et al. | |
| 5,540,734 A | 7/1996 | Zabara | |
| 5,543,588 A | 8/1996 | Bisset et al. | |
| 5,543,589 A | 8/1996 | Buchana et al. | |
| 5,556,421 A | 9/1996 | Prutchi et al. | |
| 5,556,760 A | 9/1996 | Nakamura et al. | |
| 5,565,632 A | 10/1996 | Ogawa | |
| 5,568,809 A | 10/1996 | Ben-Haim | |
| 5,571,143 A | 11/1996 | Hoegnelid et al. | |
| 5,571,997 A | 11/1996 | Gray et al. | |
| 5,578,061 A | 11/1996 | Stroetmann et al. | |
| 5,584,803 A | 12/1996 | Stevens et al. | |
| 5,584,804 A | 12/1996 | Klatz et al. | |
| 5,584,868 A | 12/1996 | Salo et al. | |
| 5,587,200 A | 12/1996 | Lorenz et al. | |
| 5,589,856 A | 12/1996 | Stein et al. | |
| 5,601,609 A | 2/1997 | Duncan | |
| 5,601,611 A | 2/1997 | Fayram et al. | |
| 5,622,687 A | 4/1997 | Krishnan et al. | |
| 5,626,622 A | 5/1997 | Cooper | |
| 5,632,267 A | 5/1997 | Högnelid et al. | |
| 5,634,899 A | 6/1997 | Shapland et al. | |
| 5,649,966 A | 7/1997 | Noren et al. | |
| 5,651,378 A | 7/1997 | Matheny et al. | |
| 5,662,687 A | 9/1997 | Hedberg et al. | |
| 5,670,755 A | 9/1997 | Kwon | |
| 5,674,251 A | 10/1997 | Combs et al. | |
| 5,674,259 A | 10/1997 | Gray | |
| 5,683,431 A | 11/1997 | Wang | |

| Patent No. | Date | Inventor |
|---|---|---|
| 5,687,734 A | 11/1997 | Dempsey et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben-Haim |
| 5,738,105 A | 4/1998 | Kroll |
| 5,741,211 A | 4/1998 | Renirie et al. |
| 5,741,791 A | 4/1998 | Olsen |
| 5,749,906 A | 5/1998 | Kieval et al. |
| 5,755,740 A | 5/1998 | Nappholz |
| 5,777,607 A | 7/1998 | Koolen |
| 5,782,876 A | 7/1998 | Flammang |
| 5,782,881 A | 7/1998 | Lu et al. |
| 5,790,106 A | 8/1998 | Hirano et al. |
| 5,792,189 A * | 8/1998 | Gray et al. ............ 607/5 |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,824,016 A * | 10/1998 | Ekwall ............ 607/9 |
| 5,825,352 A | 10/1998 | Bisset et al. |
| 5,841,078 A | 11/1998 | Miller et al. |
| 5,844,506 A | 12/1998 | Binstead |
| 5,854,881 A | 12/1998 | Yoshida et al. |
| 5,861,583 A | 1/1999 | Schediwy et al. |
| 5,865,787 A | 2/1999 | Shapland et al. |
| 5,871,506 A | 2/1999 | Mower |
| 5,906,607 A | 5/1999 | Taylor et al. |
| 5,913,876 A | 6/1999 | Taylor et al. |
| 5,919,216 A * | 7/1999 | Houben et al. ............ 607/72 |
| 5,927,284 A | 7/1999 | Borst et al. |
| 5,956,020 A | 9/1999 | D'Amico et al. |
| 5,991,649 A | 11/1999 | Garfield et al. |
| 5,995,872 A * | 11/1999 | Bourgeois ............ 607/40 |
| 6,006,134 A | 12/1999 | Hill et al. |
| 6,026,326 A * | 2/2000 | Bardy ............ 607/40 |
| 6,032,074 A | 2/2000 | Collins |
| 6,032,672 A | 3/2000 | Taylor |
| 6,037,882 A | 3/2000 | Levy |
| 6,041,252 A | 3/2000 | Walker et al. |
| 6,067,470 A | 5/2000 | Mower |
| 6,071,305 A | 6/2000 | Brown et al. |
| 6,086,582 A | 7/2000 | Altman et al. |
| 6,093,167 A | 7/2000 | Houben et al. |
| 6,122,536 A * | 9/2000 | Sun et al. ............ 600/341 |
| 6,128,007 A | 10/2000 | Seybold et al. |
| 6,133,906 A | 10/2000 | Geaghan |
| 6,135,978 A * | 10/2000 | Houben et al. ............ 604/66 |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,185,452 B1 * | 2/2001 | Schulman et al. ............ 604/20 |
| 6,236,887 B1 | 5/2001 | Ben-Haim et al. |
| 6,239,389 B1 | 5/2001 | Allen et al. |
| 6,243,607 B1 * | 6/2001 | Mintchev et al. ............ 607/40 |
| 6,261,280 B1 * | 7/2001 | Houben et al. ............ 604/500 |
| 6,278,443 B1 | 8/2001 | Amro et al. |
| 6,292,693 B1 | 9/2001 | Darvish et al. |
| 6,295,470 B1 | 9/2001 | Mower |
| 6,298,268 B1 | 10/2001 | Ben-Haim et al. |
| 6,317,631 B1 | 11/2001 | Ben-Haim et al. |
| 6,337,995 B1 | 1/2002 | Mower |
| 6,341,235 B1 | 1/2002 | Mower |
| 6,343,232 B1 | 1/2002 | Mower |
| 6,363,279 B1 | 3/2002 | Ben-Haim et al. |
| 6,392,636 B1 | 5/2002 | Ferrari et al. |
| 6,411,847 B1 | 6/2002 | Mower |
| 6,415,178 B1 | 7/2002 | Ben-Haim et al. |
| 6,417,846 B1 | 7/2002 | Lee |
| 6,424,864 B1 | 7/2002 | Matsuura |
| 6,433,069 B1 | 8/2002 | Oeltjen et al. |
| 6,449,511 B1 * | 9/2002 | Mintchev et al. ............ 607/40 |
| 6,452,514 B1 | 9/2002 | Philipp |
| 6,453,199 B1 * | 9/2002 | Kobozev ............ 607/40 |
| 6,469,719 B1 | 10/2002 | Kino et al. |
| 6,473,069 B1 | 10/2002 | Gerpheide |
| 6,504,530 B1 | 1/2003 | Wilson et al. |
| 6,505,745 B1 | 1/2003 | Anderson |
| 6,507,093 B2 | 1/2003 | Kaneda et al. |
| 6,555,235 B1 | 4/2003 | Aufderheide et al. |
| RE38,119 E | 5/2003 | Mower |
| 6,558,345 B1 | 5/2003 | Houben et al. |
| 6,570,557 B1 | 5/2003 | Westerman et al. |
| 6,571,127 B1 | 5/2003 | Ben-Haim et al. |
| 6,572,542 B1 * | 6/2003 | Houben et al. ............ 600/300 |
| 6,583,676 B2 | 6/2003 | Krah et al. |
| 6,587,093 B1 | 7/2003 | Shaw et al. |
| 6,605,039 B2 | 8/2003 | Houben et al. |
| 6,611,258 B1 | 8/2003 | Tanaka et al. |
| 6,612,983 B1 * | 9/2003 | Marchal ............ 600/300 |
| 6,633,280 B1 | 10/2003 | Matsumoto et al. |
| 6,652,444 B1 | 11/2003 | Ross |
| 6,667,740 B2 | 12/2003 | Ely et al. |
| 6,690,156 B1 | 2/2004 | Weiner et al. |
| 6,762,752 B2 | 7/2004 | Perski et al. |
| 6,853,862 B1 | 2/2005 | Marchal et al. |
| 7,006,871 B1 | 2/2006 | Darvish et al. |
| 7,076,306 B2 | 7/2006 | Marchal et al. |
| 7,440,806 B1 | 10/2008 | Whitehurst et al. |
| 2002/0026141 A1 | 2/2002 | Houben et al. |
| 2002/0032444 A1 | 3/2002 | Mische |
| 2002/0161414 A1 | 10/2002 | Flesler et al. |
| 2003/0018367 A1 | 1/2003 | DiLorenzo |
| 2003/0040777 A1 | 2/2003 | Shemer et al. |
| 2003/0055464 A1 | 3/2003 | Darvish et al. |
| 2003/0055466 A1 | 3/2003 | Ben-Haim et al. |
| 2003/0055467 A1 | 3/2003 | Ben-Haim et al. |
| 2003/0181958 A1 | 9/2003 | Dobak, III |
| 2003/0188899 A1 | 10/2003 | Chao et al. |
| 2003/0208242 A1 | 11/2003 | Harel et al. |
| 2004/0044376 A1 | 3/2004 | Flesler et al. |
| 2004/0059393 A1 | 3/2004 | Policker et al. |
| 2004/0105040 A1 | 6/2004 | Oh et al. |
| 2004/0147816 A1 | 7/2004 | Policker et al. |
| 2004/0155871 A1 | 8/2004 | Perski et al. |
| 2004/0249421 A1 | 12/2004 | Harel et al. |
| 2005/0065553 A1 | 3/2005 | Ben Ezra et al. |
| 2006/0074459 A1 | 4/2006 | Flesler et al. |
| 2006/0085045 A1 | 4/2006 | Harel et al. |
| 2006/0097991 A1 | 5/2006 | Hotelling et al. |
| 2006/0184207 A1 | 8/2006 | Darvish et al. |
| 2007/0016262 A1 | 1/2007 | Gross et al. |
| 2007/0027490 A1 | 2/2007 | Ben-Haim et al. |
| 2007/0027493 A1 | 2/2007 | Ben-Haim et al. |
| 2007/0051849 A1 | 3/2007 | Watts et al. |
| 2007/0060812 A1 | 3/2007 | Harel et al. |
| 2007/0060971 A1 | 3/2007 | Glasberg et al. |
| 2007/0092446 A1 | 4/2007 | Haddad et al. |
| 2007/0156177 A1 | 7/2007 | Harel et al. |
| 2007/0161851 A1 | 7/2007 | Takizawa et al. |
| 2007/0171211 A1 | 7/2007 | Perski et al. |
| 2007/0179556 A1 | 8/2007 | Ben Haim et al. |
| 2007/0185540 A1 | 8/2007 | Ben-Haim et al. |
| 2007/0239216 A9 | 10/2007 | Shemer et al. |
| 2007/0293901 A1 | 12/2007 | Rousso et al. |
| 2007/0299320 A1 | 12/2007 | Policker et al. |
| 2008/0058879 A1 | 3/2008 | Ben-Haim et al. |
| 2008/0058889 A1 | 3/2008 | Ben-Haim et al. |
| 2008/0058891 A1 | 3/2008 | Ben-Haim et al. |
| 2008/0065159 A1 | 3/2008 | Ben-Haim et al. |
| 2008/0065163 A1 | 3/2008 | Ben-Haim et al. |
| 2008/0065164 A1 | 3/2008 | Ben-Haim et al. |
| 2008/0065168 A1 | 3/2008 | Bitton et al. |
| 2008/0077174 A1 | 3/2008 | Mische |
| 2008/0178684 A1 | 7/2008 | Spehr |
| 2008/0188837 A1 | 8/2008 | Belsky et al. |
| 2009/0062893 A1 | 3/2009 | Spehr et al. |
| 2009/0088816 A1 | 4/2009 | Harel et al. |
| 2009/0118797 A1 | 5/2009 | Kliger et al. |
| 2009/0131993 A1 | 5/2009 | Rousso et al. |
| 2009/0204063 A1 | 8/2009 | Policker et al. |
| 2009/0281449 A1 | 11/2009 | Thrower et al. |
| 2009/0292324 A1 | 11/2009 | Rousso et al. |

| | | | |
|---|---|---|---|
| 2010/0016923 | A1 | 1/2010 | Rousso et al. |
| 2010/0228105 | A1 | 9/2010 | Policker et al. |
| 2010/0305468 | A1 | 12/2010 | Policker et al. |
| 2010/0324644 | A1 | 12/2010 | Levi et al. |

FOREIGN PATENT DOCUMENTS

| | | |
|---|---|---|
| EP | 0156593 | 10/1985 |
| EP | 0250931 | 1/1988 |
| EP | 0314078 | 5/1989 |
| EP | 0481684 | 4/1992 |
| EP | 0528751 | 2/1993 |
| EP | 0220916 | 4/1994 |
| EP | 0727241 | 8/1996 |
| EP | 1263498 | 12/2002 |
| EP | 0910429 | 3/2005 |
| GB | 1 394 171 | 5/1975 |
| GB | 2280377 | 2/1995 |
| JP | 62-112530 | 5/1987 |
| JP | 62-275471 | 11/1987 |
| JP | 04-117967 | 4/1992 |
| JP | 04117967 | 4/1992 |
| JP | 04-282168 | 10/1992 |
| JP | 04-365493 | 12/1992 |
| JP | 4365493 | 12/1992 |
| JP | 06-169998 | 6/1994 |
| JP | 06-506619 | 7/1994 |
| JP | 07-503865 | 4/1995 |
| JP | 07-126600 | 5/1995 |
| JP | 7126600 | 5/1995 |
| JP | 07-144024 | 6/1995 |
| JP | 08-243176 | 9/1996 |
| JP | 8243176 | 9/1996 |
| RU | 2014844 | 6/1994 |
| RU | 1827793 | 5/1995 |
| RU | 2055606 | 3/1996 |
| RU | 2075980 | 3/1997 |
| RU | 2077273 | 4/1997 |
| RU | 2078547 | 5/1997 |
| SU | 386634 | 8/1972 |
| SU | 553977 | 5/1975 |
| SU | 831131 | 4/1979 |
| WO | WO 91/19534 | 12/1991 |
| WO | WO 92/00716 | 1/1992 |
| WO | WO 93/02743 | 2/1993 |
| WO | WO 93/02745 | 2/1993 |
| WO | WO 93/18820 | 9/1993 |
| WO | WO 94/17855 | 8/1994 |
| WO | WO 95/02995 | 2/1995 |
| WO | WO 95/08316 | 3/1995 |
| WO | WO 96/10358 | 4/1996 |
| WO | WO 97/15227 | 5/1997 |
| WO | WO 97/25098 | 7/1997 |
| WO | WO 97/25101 | 7/1997 |
| WO | WO 97/26042 | 7/1997 |
| WO | WO 97/27900 | 8/1997 |
| WO | WO 97/29679 | 8/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/56378 | 12/1998 |
| WO | WO 98/57701 | 12/1998 |
| WO | WO 99/03533 | 1/1999 |
| WO | WO 9903533 * | 1/1999 |
| WO | WO 97/24981 | 7/1999 |
| WO | WO 00/04947 | 2/2000 |
| WO | WO 00/27475 | 5/2000 |
| WO | WO 00/42914 | 7/2000 |
| WO | WO 00/53257 | 9/2000 |
| WO | WO 00/61223 | 10/2000 |
| WO | WO 01/10375 | 2/2001 |
| WO | WO 01/49367 | 7/2001 |
| WO | WO 01/52931 | 7/2001 |
| WO | WO 01/66183 | 9/2001 |
| WO | WO 01/91854 | 12/2001 |
| WO | WO 01/93950 | 12/2001 |
| WO | WO 01/93951 | 12/2001 |
| WO | WO 02/10791 | 2/2002 |
| WO | WO 02/053093 | 7/2002 |
| WO | WO 02/082968 | 10/2002 |
| WO | WO 03/045493 | 6/2003 |
| WO | WO 2004/021858 | 3/2004 |
| WO | WO 2004/070396 | 8/2004 |
| WO | WO 2004/112563 | 12/2004 |
| WO | WO 2004/112883 | 12/2004 |
| WO | WO 2005/007232 | 1/2005 |
| WO | WO 2005/023081 | 3/2005 |
| WO | WO 2005/087310 | 9/2005 |
| WO | WO 2005/114369 | 12/2005 |
| WO | WO 2006/018851 | 2/2006 |
| WO | WO 2006/087712 | 8/2006 |
| WO | WO 2006/087717 | 8/2006 |
| WO | WO 2006/097934 | 9/2006 |
| WO | WO 2006/102626 | 9/2006 |
| WO | WO 2006/129321 | 9/2006 |
| WO | WO 2007/080595 | 7/2007 |
| WO | WO 2007/091255 | 8/2007 |
| WO | WO 2008/117296 | 10/2008 |
| WO | WO 2008/139463 | 11/2008 |
| WO | WO 2011/092710 | 8/2011 |

OTHER PUBLICATIONS

Official Action Dated Jan. 13, 2011 From the US Patent and Trademark Office Re.: U.S. Appl. No. 11/931,889.
Official Action Dated Dec. 14, 2010 From the US Patent and Trademark Office Re.: U.S. Appl. No. 11/884,389.
Bakker et al. "Beneficial Effects of Biventricular Pacing of Congestive Heart Failure", Pace, 17(Part II): 318, 1994.
Bakker et al. "Biventricular Pacing Improves Functional Capacity in Patients With End-Stage Congestive Heart Failure", Pace, 17(11/Part II/120): 825, 1995.
Bargheer et al. "Prolongation of Monophastic Action Potantial Duration and the Refractory Period in the Human Heart by Tedisamil, A New Potassium-Blocking Agent", The European Society of Cardiology, 15(10): 1409-1414, 1994.
Burfeind et al. "The Effects of Mechanical Cardiac Stabilization on Left Ventricular Performance", European Journal of Cardio-Thoracic Surgery,14: 285-289, 1998.
Cazeau et al. "Multisite Pacing for End-Stage Heart Failure: Early Experience", PACE, 19(Part II): 1748-1757, 1996.
Cheng et al. "Calcium Sparks: Elementary Events Underlying Excitation-Contraction Coupling in Heart Muscle", Science, 262: 740-744, 1993.
Cooper "Postextrasystolic Potentiation: Do We Really Know What It Means and How to Use It?", Circulation, 88(6): 2962-2971, 1993.
Coulton et al. "Magnetic Fields and Intracellular Calcium: Effects on Lymphocytes Exposed to Conditions for 'Cyclotron Resonance'", Physics in Medicine and Biology, 38: 347-360, 1993.
Crider et al. "2-Pyridylthioureas: Novel Nonpeptide Somatostatin Agonists With SST4 Selectivity", Current Pharmaceutical Design, 5 (4: p. 255-263, 1999. Abstract only.
Dillion "Optial Recordings in the Rabbit Heart Show That Defibrillation Strenght Shocks Prolong the Duration of Depolarization and the Refractory Period", Circulation Research, 69: 842-856, 1991.
Erol-Yilmaz et al. "Reversed Remodelling of Dilated Left Sided Cardiomyopathy After Upgrading From VVIR to VVIR Biventricular Pacing", Europace, 4: 445-449, 2002.
Fain et al. "Improved Internal Defibrillation Efficacy With A Biphasic Waveform", American Heart Journal, 117(2): 358-364, 1989.
Fleg et al. "Impact of Age on the Cardiovasvular Response to Dynamic Upright Exercise in Healthy Men and Women", Journal of Applied Physiology, 78: 890-900, 1995.
Foster et al. "Acute Hemodynamic Effects of Atrio—Biventricular Padng in Humans", The Society of Thoracic Surgeons, 59: 294-300, 1995.
Franz "Bridging the Gap Between Basic Clinical Electrophysiology: What Can Be Learned From Monophasic Action Potential Recordings?", Journal of Cardiovascular Electrophysiology, 5(8): 699-710, 1994.
Franz "Method and Theory of Monophasic Action Potential Recording", Progresses in Cardiovascular Diseases, 33(6): 347-368, 1991.

Fromer et al. "Ultrarapid Subthreshold Stimulation for Termination of Atriventricular Node Reentrant Tachycardia", Journal of the American College of Cardiology, 20(4): 879-883, 1992.

Fu et al. "System Identification of Electrically Coupled Smooth Muscle Cells: The Passive Electrically Coupled Smooth Muscle Cells: The Passive Electrical Properties", IEEE Transactions on Biomedical Engineering, 38(11): 1130-1140, 1991.

Gill et al. "Refractory Period Extension During Ventricular Pacing at Fibrillatory Pacing Rates", PACE, 20(Part I): 647-653, 1997.

Gilmour Jr. et al. "Dynamics of Circus Movement Re-Entry Across Canine Purkinje Fibre-Muscle Junctions", The Journal of Physiology, 476(3): 473-485, 1994.

Gilmour Jr. et al. "Overdrive Suppression of Conduction at the Canine Purkinje-Muscle Junction", Circulation, 76(6): 1388-1396, 1987.

Hoffman et al. "Effects of Postextrasystolic Potentiation on Normal and Failing Hearts", Bulletin of the New York Academy of Medicine, 41(5): 498-534, 1965.

Horner et al. "Electrode for Recording Direction of Activation, Conduction Velocity, and Monophasic Action Potential of Myocardium", American Journal of Physiology, 272: H1917-H1927, 1997.

King et al. "The Inotropic Action of Paired Pulse Stimulation in the Normal and Failing Heart: An Experimental Study", Cardiovascular Research, 2: 122-129, 1968.

Knisley et al. "Effect of Field Stimulation on Cellular Repolarization in Rabbit Myocardium Implications for Reentry Induction", Circulation Research, 70: 707-715, 1991.

Knisley et al. "Prolongation and Shortening of Action Potentials by Electrical Shocks in Frog Ventricular Muscle", American Journal of Physiology, 266: H2348-H2358, 1994.

Koller et al. "Relation Between Repolarization and Refractoriness During Programmed Electrical Stimulation in the Human Right Ventricle", Circulation, 91: 2378-2384, 1995.

Langberg et al. "Identification of Ventricular Tachycardia With Use of the Morphology of the Endocardial Electrogram", Circulation, 77: 1363-1369, 1988.

Lindström et al. "Intracellular Calcium Oscillations in a T-Cell Line After Exposure to Extremely-Low-Frequency Magnetic Fields With Variable Frequencies and Flux Densities", Bioelectromagnetics, 16: 41-47, 1995.

Mercando et al. "Automated Detection of Tachycardias by Antitachycardia Devices", Cardiac Electrophysiology: From Cell to Bedside, Chap.100: 943-948, 2004.

Miledi et al. "Effects of Membrane Polarization on Sarcoplasmic Calcium Release in Skeletal Muscle", Proceedings of the Royal Society of London B: Biological Science, 213(1190): 1-13, 1981. Abstract.

Paul et al. "Automatic Recognition of Ventricular Arrhythmias Using Temporal Electrogram Analysis", PACE, 14: 1265-1273, 1991.

Pumir et al. "Control of Rotating Waves in Cardiac Muscle: Analysis of the Effect of Electric Field", Proceedings of the Royal Society B: Biological Sciences, 257(1349): 129-134, 1994.

Saihara "Summation of Excitation With a Single Conditioning Stimulus in the Canine Heart", PACE, 13: 52-58, 1990.

Sakuma et al. "A Model Analysis of Aftereffects of High-Intensity DC Stimulation on Action Potential of Ventricular Muscle", IEEE Transactions on Biomedical Engineering, 45(2): 258-267, 1998.

Skale et al. "Inhibition of Premature Ventricular Extrastimuli by Subthreshold Conditioning Stimuli", Journal of the American College of Cardiology, 6(1): 133-140, 1985.

Sukhorukov et al "The Effect of Electrical Deformation Forces on the Electropermeabilization of Erythrocyte Membranes in Low-and High-Conductivity Media", The Journal of Membrane Biology, 163(3): 235-245, 1998.

Sweeney et al. "Refractory Interval After Transcardiac Shocks During Ventricular Fibrillation", Circulation, 94: 2947-2952, 1996.

Sweeney et al. "Ventricular Refractory Period Extension Caused by Defibrillation Shocks", Circulation, 82: 965-972, 1990.

Sweeny et al. "Countershock Strength-Duration Relationship for Myocardial Refractory Period Extension", Academy of Emergency Medicine, 2: 57-62, 1995.

Swerdlow et al. "Cardiovascular Collapse Caused by Electrocardiographically Silent 60-Hz Intracardiac Leakage Current: Implications for Electrical Safety", Circulation, 99: 2559-2564, 1999.

Talit et al. "The Effect of External Cardiac Pacing on Stroke Volume", PACE, 13: 598-602, 1990.

Taniguchi et al. "Inhomogeneity of Cellular Activation Time and VMax in Normal Myocardial Tissue Under Electrical Field Stimulation", American Journal of Physiology, 267: H694-H705, 1994.

Thakor et al. "Effect of Varying Pacing Waveform Shapes on Propagation and Hemodynamics in the Rabbit Heart", American Journal of Cardiology, 79(6A): 36-43, 1997.

Tsong "Electroporation of Cell Membranes", Biophysical Journal, 60: 297-306, 1991.

Wessale et al. "Stroke Volume and the Three Phase Cardiac Output Rate Relationship With Ventricular Pacing", PACE, 13: 673-680, 1990.

Wirtzfeld et al. "Physiological Pacing: Present Status and Future Developments", PACE, 10(Pt.I): 41-57, 1987.

Yokoyama "The Phase of Supernormal Excitation in Relation to the Strength of Subthreshold Stimuli", Japanese Heart Journal, 17(3): 315-325, 1975.

Office Action Dated Nov. 2, 2007 From the Patent Office of the People's Republic of China Re.: Application No. 2004800009336.9.

Official Action Dated Dec. 5, 2008 From the US Patent and Trademark Office Re.: U.S. Appl. No. 11/550,560.

Official Action Dated Dec. 8, 2008 From the US Patent and Trademark Office Re.: U.S. Appl. No. 10/804,560.

Official Action Dated Dec. 24, 2008 From the US Patent and Trademark Office Re.: U.S. Appl. No. 10/237,263.

Supplementary European Search Report and the European Search Opinion Dated Nov. 28, 2008 From the European Patent Office Re.: Application No. 006759102.4.

Translation of the Examination Report Dated Apr. 3, 2008 From the Government of India, Patent Office Re.: Application No. 1821/CHENP/2005.

Supplementary European Search Report Dated Jan. 12, 2011 From the European Patent Office Re. Application No. 05718889.8.

Official Action Dated Mar. 10, 2011 From the US Patent and Trademark Office Re.: U.S. Appl. No. 11/884,389.

Examination Report Dated Mar. 13, 2012 From the Government of India, Patent Office, Intellectual Property Building Re. Application No. 2988/CHENP/2007.

Communication Pursuant to Article 94(3) EPC Dated Jan. 27, 2010 From the European Patent Office Re. Application No. 07110023.4.

Communication Pursuant to Article 96(2) EPC Dated Mar. 2, 2007 From the European Patent Office Re.: Application No. 97929478.2.

Communication to Pursuant to Article 94(3) EPC Dated Mar. 4, 2009 From the European Search Report Re.: Application No. 06759102.4.

International Search Report and the Written Opinion Dated May 12, 2006 From the International Searching Authority Re.: Application No. PCT/US05/44557.

International Search Report and the Written Opinion Dated Oct. 16, 2006 From the International Searching Authority Re.: Application No. PCT/US06/17281.

Office Action Dated Dec. 4, 2009 From the State Intellectual Property Office of the People's Republic of China Re.: Application No. 03824661.9 and Its Translation Into English.

Office Action Dated Jan. 8, 2010 From the State Intellectual Property Office (SIPO) of the People's Republic of China Re.: Application No. 200480012687.5 and Its Translation Into English.

Official Action Dated Jun. 1, 2009 From the US Patent and Trademark Office Re.: U.S. Appl. No. 10/039,845.

Official Action Dated Oct. 1, 2009 From the US Patent and Trademark Office Re.: U.S. Appl. No. 10/237,263.

Official Action Dated Feb. 4, 2010 From the US Patent and Trademark Office Re.: U.S. Appl. No. 10/039,845.

Official Action Dated Jan. 5, 2010 From the US Patent and Trademark Office Re.: U.S. Appl. No. 11/802,685.

Official Action Dated Nov. 5, 2010 From the US Patent and Trademark Office Re.: U.S. Appl. No. 10/549,216.

Official Action Dated Jan. 21, 2009 From the US Patent and Trademark Office Re.: U.S. Appl. No. 10/570,576.

Official Action Dated Mar. 25, 2010 From the US Patent and Trademark Office Re.: U.S. Appl. No. 10/804,560.
Request for Ex Parte Reexamination of Patent No. 6,363,279—Official Action Dated Jun. 20, 2008 From the US Patent and Trademark Office Re.: U.S. Appl. No. 90/008,688.
Request for Ex Parte Reexamination of US Patent No. 6,236,887—Notice of Intent to Issue Ex Parte Examination Certificate Dated Mar. 19, 2009 From the US Patent and Trademark Office Re.: U.S. Appl. No. 90/008,707.
Response Dated Mar. 1, 2010 to Official Action of Aug. 28, 2009 From the US Patent and Trademark Office Re.: U.S. Appl. No. 11/932,064.
Response Dated Feb. 2, 2010 to Official Action of Dec. 2, 2009 From the US Patent and Trademark Office Re.: U.S. Appl. No. 11/932,149.
Response Dated Mar. 3, 2010 to Official Action of Sep. 3, 2009 From the US Patent and Trademark Office Re.: U.S. Appl. No. 10/804,560.
Response Dated Feb. 4, 2010 to Official Action of Dec. 4, 2009 From the US Patent and Trademark Office Re.: U.S. Appl. No. 11/884,389.
Response Dated Mar. 4, 2010 to Official Action of Nov. 5, 2010 From the US Patent and Trademark Office Re.: U.S. Appl. No. 10/549,216.
Response Dated Apr. 6, 2010 to Official Action of Oct. 6, 2009 From the US Patent and Trademark Office Re.: U.S. Appl. No. 11/550,560.
Response Dated Feb. 7, 2010 to Official Action of Dec. 2, 2009 From the US Patent and Trademark Office Re.: U.S. Appl. No. 11/932,149.
Response Dated Feb. 7, 2010 to Official Action of Nov. 3, 2009 From the US Patent and Trademark Office Re.: U.S. Appl. No. 11/931,724.
Response Dated Feb. 8, 2010 to Official Action Dated Oct. 1, 2009 From the US Patent and Trademark Office Re.: U.S. Appl. No. 10/237,263.
Response Dated Feb. 9, 2010 to Official Action of Oct. 8, 2009 From the US Patent and Trademark Office Re.: U.S. Appl. No. 10/116,201.
Response Dated Mar. 15, 2010 to Official Action of Sep. 14, 2009 From the US Patent and Trademark Office Re.: U.S. Appl. No. 11/931,889.
Response Dated Feb. 18, 2010 to Official Action of Aug. 18, 2009 From the US Patent and Trademark Office Re.: U.S. Appl. No. 10/570,576.
Response Dated Nov. 22, 2009 to Official Action of Jun. 1, 2009 From the US Patent and Trademark Office Re.: U.S. Appl. No. 10/039,845.
Response Dated Mar. 25, 2010 to Official Action of Sep. 25, 2009 From the US Patent and Trademark Office Re.: U.S. Appl. No. 10/526,708.
Patterson et al. "Therapeutic Angiogenesis: The New Electrophysiology?", Circulation, 99(20): 2614-2616, 1999.
Schirra et al. "Exendin(9-39) Amide Is An Antagonist of Glucagon-Like Peptide-1(7-36) Amide in Humans", Journal of Clinical Investigation, 101(7): 1421-1430, Apr. 1998.
Todd et al. "Subcutaneous Glucagon-Like Peptide I Improves Postprandial Glycaemic Control Over a 3-Week Period in Patients With Early Type 2 Diabetes", Clinical Science, 95: 325-329, 1998.
Official Action Dated Mar. 31, 2010 From the US Patent and Trademark Office Re.: U.S. Appl. No. 10/237,263.
Office Action Dated Jul. 13, 2009 From the State Intellectual Property Office of the People's Republic of China Re.: Application No. 200480027083.3 and Its Translation Into English.
Official Action Dated Dec. 2, 2009 From the US Patent and Trademark Office Re.: U.S. Appl. No. 11/932,149.
Official Action Dated Sep. 3, 2009 From the US Patent and Trademark Office Re.: U.S. Appl. No. 10/804,560.
Official Action Dated Dec. 4, 2009 From the US Patent and Trademark Office Re.: U.S. Appl. No. 11/884,389.
Official Action Dated Oct. 6, 2009 From the US Patent and Trademark Office Re.: U.S. Appl. No. 11/550,560.
Official Action Dated Oct. 8, 2009 From the US Patent and Trademark Office Re.: U.S. Appl. No. 10/116,201.
Official Action Dated Sep. 14, 2009 From the US Patent and Trademark Office Re.: U.S. Appl. No. 11/931,889.
Official Action Dated Aug. 18, 2009 From the US Patent and Trademark Office Re.: U.S. Appl. No. 10/570,576.
Official Action Dated Sep. 25, 2009 From the US Patent and Trademark Office Re.: U.S. Appl. No. 10/526,708.
Official Action Dated Aug. 28, 2009 From the US Patent and Trademark Office Re.: U.S. Appl. No. 11/802,685.
Official Action Dated Aug. 28, 2009 From the US Patent and Trademark Office Re.: U.S. Appl. No. 11/932,064.
Gardner "Natriuretic Peptides: Markers or Modulators of Cardiac Hypertrophy?", Trends in Endocrinology and Metabolism, 14(9): 411-416, Nov. 2003.
Response Dated Feb. 24, 2011 to Notice of Allowance of Nov. 29, 2010 From the US Patent and Trademark Office Re. U.S. Appl. No. 10/237,263.
Official Action Dated Apr. 27, 2010 From the US Patent and Trademark Office Re.: U.S. Appl. No. 10/570,576.
Blank et al. "Initial Interactions in Electromagnetic Field-Induced Biosynthesis", Journal of Cellular Physiology, 199: 359-363, 2004.
Response Dated May 6, 2010 to Office Action Dated Jan. 8, 2010 From the State Intellectual Property Office (SIPO) of the People's Republic of China Re.: Application No. 200480012687.5.
Notice of Allowance Dated May 11, 2011 From the US Patent and Trademark Office Re.: U.S. Appl. No. 10/237,263.
Official Action Dated May 11, 2011 From the US Patent and Trademark Office Re.: U.S. Appl. No. 10/804,560.
Examination Report Dated Nov. 30, 2010 From the Government of India, Patent Office Re. Application No. 212/MUMNP/2006.
International Search Report and the Written Opinion Dated Sep. 29, 2006 From the International Searching Authority Re.: Application No. PCT/IL06/00204.
International Search Report Dated Sep. 13, 2004 From the International Searching Authority Re.: Application No. PCT/IL03/00736.
Notice of Allowance Dated Sep. 7, 2006 From the US Patent and Trademark Office Re.: U.S. Appl. No. 10/804,560.
Notice of Allowance Dated Nov. 29, 2010 From the US Patent and Trademark Office Re. U.S. Appl. No. 10/237,263.
Office Action Dated Apr. 13, 2010 From the State Intellectual Property Office of the People's Republic of China Re. Application No. 200480027293.3 and Its Translation Into English.
Official Action Dated Dec. 3, 2009 From the US Patent and Trademark Office Re.: U.S. Appl. No. 11/318,845.
Official Action Dated Jan. 4, 2011 From the US Patent and Trademark Office Re.: U.S. Appl. No. 11/318,845.
Official Action Dated May 5, 2010 From the US Patent and Trademark Office Re.: U.S. Appl. No. 11/884,389.
Official Action Dated Jul. 9, 2007 From the US Patent and Trademark Office Re.: U.S. Appl. No. 10/237,263.
Official Action Dated Sep. 11, 2008 From the US Patent and Trademark Office Re.: U.S. Appl. No. 10/237,263.
Official Action Dated Dec. 15, 2010 From the US Patent and Trademark Office Re.: U.S. Appl. No. 10/804,560.
Official Action Dated Apr. 18, 2007 From the US Patent and Trademark Office Re.: U.S. Appl. No. 10/804,560.
Official Action Dated May 26, 2010 From the US Patent and Trademark Office Re.: U.S. Appl. No. 11/318,845.
Official Action Dated Jul. 31, 2008 From the US Patent and Trademark Office Re.: U.S. Appl. No. 11/318,845.
Response Dated May 3, 2010 to Official Action of Dec. 3, 2009 From the US Patent and Trademark Office Re.: U.S. Appl. No. 11/318,845.
Response Dated Oct. 5, 2010 to Official Action of May 5, 2010 From the US Patent and Trademark Office Re.: U.S. Appl. No. 11/884,389.
Response Dated Aug. 26, 2010 to Official Action of May 26, 2010 From the US Patent and Trademark Office Re.: U.S. Appl. No. 11/318,845.
Response Dated Jan. 27, 2011 to Official Action of Sep. 27, 2010 From the US Patent and Trademark Office Re.: U.S. Appl. No. 10/804,560.
Supplemental Response Dated Mar. 28, 2010 After an Interview of Mar. 4, 2010 From the US Patent and Trademark Office Re. U.S. Appl. No. 10/237,263.
Supplementary Notice of Allowability Dated Nov. 22, 2006 From the US Patent and Trademark Office Re.: U.S. Appl. No. 10/804,560.
Translation of Notification of Reasons of Rejection Dated Apr. 12, 2010 From the Japanese Patent Office Re.: Application No. 2006-525265.

Antoni et al. "Polarization Effects of Sinusoidal 50-Cycle Alternating Current on Membrane Potential of Mammalian Cardiac Fibres", Pfl?gers Archiv European Journal of Physiology, 314(4): 274-291, 1970. Abstract.

Bers "Excitation Contraction Coupling and Cardiac Contractile Force", Internal Medicine, 237(2): 17, 1991, Abstract.

Bouaziz et al. "Direct Electrical Stimulation of Insulin Secretion by Intact Murine Islets of Langerhans Through the Culture Support", Electromagnetic Biology and Medicine, 17(2): 171-184, 1998. Abstract.

Bronzino "Biomedical Engineering Handbook", IEEE Press/CRC Press, Chap. 82.5: 1288, 1995.

Fleg et al. "Impact of Age on the Cardiovasvular Response to Dynamic Upright Exercise in Healthy Men and Women", Journal of Applied Physiologyl, 78: 890-900, 1995, Abstract.

Franz "Method and Theory of Monophasic Action Potential Recording", Progress in Cardiovascular Diseases, 33(6): 347-368, 1991. Abstract.

Knisley et al. "Effect of Field Stimulation on Cellular Repolarization in Rabbit Myocardium. Implications for Reentry Induction", Circulation Research, 70(4): 707-715, Apr. 1992.

Knisley et al. "Prolongation and Shortening of Action Potentials by Electrical Shocks in Frog Ventricular Muscle", American Journal of Physiology, 266(6): H2348-H2358, 1994, Abstract.

Lindstr?m et al. "Intracellular Calcium Oscillations in a T-Cell Line After Exposure to Extremely-Low-Frequency Magnetic Fields with Variable Frequencies and Flux Densities", Bioelectromagnetics, 16(1): 41-47, 1995, Abstract.

Loginov et al. "Effects of an Impulse Electromagnetic Field on Calcium Ion Accumulation in the Sarcoplasmic . . . ", Kosm. Biol. Aviakosm. Med., 15: 51-53, 1991.

Lubart et al. "Effect of Light on Calcium Transport in Bull Sperm Cells", Journal of Photochemistry and Photobiology B, Biology, 15(4): 337-341, Sep. 15, 1992. Abstract.

Pumir et al. "Control of Rotating Waves in Cardiac Muscle: Analysis of the Effect of Electric Fields", Proceedings of the Royal Society B: Biological Sciences, 257(1349): 129-134, 1994. Abstract.

Saveliev et al. "Guidebook on Clinical Endoscopy", Moscow Medicine, p. 21, 35, Extract, 1985.

Skale et al "Inhibition of Premature Ventricular Extrastimuli by Subthreshold Conditioning Stimuli", Journal of the American College of Cardiology, 6: 133-140, 1985. Abstract.

Solomonow et al. "Control of Muscle Contractile Force Through Indirect High-Frequency Stimulation", American Journal of Physical Medicine, 62(2): 71-82, Apr. 1983. Abstract.

Stevenson et al. "Electrophysiologic Characteristics of Ventricular Tachycardia or Fibrillation in Relation to Age of Myocardial Infarction", The American Journal of Cardiology, 57(6): 387-391, Feb. 15, 1986. Abstract.

Windle et al. "Subthreshold Conditioning Stimuli Prolong Human Ventricular Refractoriness", American Journal of Cardiology, 57(6): 381-386, 1986. Abstract.

Yokoyama "The Phase of Supernormal Excitation in Relation to the Strength of Subthreshold Stimuli", Japanese Heart Journal, 17(3): 315-325, May 1976.

Notice of Allowance Dated May 27, 2010 From the US Patent and Trademark Office Re.: U.S. Appl. No. 10/549,216.

Official Action Dated Jun. 28, 2010 From the US Patent and Trademark Office Re.: U.S. Appl. No. 11/931,889.

Supplementary European Search Report Dated Jun. 7, 2010 From the European Patent Office Re. Application No. 04770468.9.

Official Action Dated Jun. 17, 2010 From the US Patent and Trademark Office Re.: U.S. Appl. No. 10/549,216.

Response Dated Jul. 1, 2010 to Invitation Pursuant to Rule 62a(1) EPC and Rule 63(1) EPC of May 5, 2010 From the European Patent Office Re.: Application No. 04719312.3.

Examination Report Dated May 18, 2011 From the Government of India, Patent Office, Intellectual Property Building Re. Application No. 2988/CHENP/2007.

Official Action Dated May 21, 2010 From the US Patent and Trademark Office Re. U.S. Appl. No. 10/116,201.

Official Action of Nov. 3, 2009 From the US Patent and Trademark Office Re.: U.S. Appl. No. 11/931,724.

Official Action of Apr. 30, 2010 From the US Patent and Trademark Office Re.: U.S. Appl. No. 11/931,724.

Official Action Dated Jun. 11, 2010 From the US Patent and Trademark Office Re.: U.S. Appl. No. 11/550,560.

Antman et al. "Treatment of 150 Cases of Life-Threatening Digitalis Intoxication With Digoxin-Specific Fab Antibody Fragments", Circulation, 81(6): 1744-1752, 1990.

Antoni et al. "Polarization Effects of Sinusoidal 50-Cycle Alternating Current on Membrane Potential of Mammalian Cardiac Fibres", Pflügers Archiv European Journal of Physiology, 314(4): 274-291, 1970. Abstract, 1970.

Bargheer et al. "Prolongation of Monophasic Action Potential Duration and the Refractory Period in the Human Heart by Tedisamil, A New Potassium-Blocking Agent", Journal European Heart, 15(10): 1409-1414, 1994, Abstract.

Bers "Excitation Contraction Coupllng and Cardiac Contractile Force", Internal Medicine, 237(2): 17, 1991, Abstract.

Borst et al. "Coronary Artery Bypass Gratting Without Cardiopulomonary Bypass and Without Interuption of Native Coronary Flow Using A Novel Anastomosis Site Restraining Device (Octupus)", Journal of the American College of Cardiology, 27(6): 1356-1364, 1996.

Cano et al. "Dose-Dependent Reversal of Dixogin-Inhibited Activity of an In-Vitro Na+K+ATPase Model by Digoxin-Specific Antibody", Toxicology Letters, 85(2): 107-1011, 1996.

Cazeau et al. "Multisite Pacing for End-Stage Heart Failure: Early Experience", Pacing and Clinical Electrophysiology, 19(11): 1748-1757, 1996, Abstract.

Cheng et al. "Calcium Sparks: Elementary Events Underlying Excitation-Contraction Coupling in Heart Muscle", Science, 262(5134): 740-744, 1993, Abstract.

Cooper "Postextrasystolic Potention. Do We Really Know What It Means and How to Use It?", Circulation, 88: 2962-2971, 1993.

Coulton et al. "Magnetic Fields and Intracellular Calcium; Effects on Lymphocytes Exposed to Conditions for 'Cyclotron Resonance'", Phys. Med. Biol., 38: 347-360, 1993, Abstract.

Dillion "Optial Recordings in the Rabbit Heart Show That Defibrillation Strength Shocks Prolong the Duration of Depolarization and the Refractory Period", Circulation Research, 69: 842-856, 1991.

Dillon "Synchronized Repolarization After Defibrillation Shocks. A Possible Component of the Defibrillation Process Demonstration by Optical Recordings in Rabbit Heart", Circulation, 85(5): 1865-1878, 1992.

Fain et al. "Improved Internal Defibrillation Efficacy With a Biphasic Waveform", American Heart Journal, 117(2): 358-364, 1989, Abstract.

Fleischhauer et al. "Electrical Resistances of Interstitial and Microvascular Space as Determinants of the Extracellular Electrical Field and Velocity of Propagation in Ventricular Myocardium", Circulation, 92: 587-594, 1995.

Foster et al. "Acute Hemodynamic Effects of Atrio—Biventricular Padng in Humans", The Society of Thoracic Surgeons, 59: 294-300, 1995, Abstract.

Franz "Bridging the Gap Between Basic Clinical Electrophysiology: What Can Be Learned From Monophasic Action Potential Recordings?", Journal Cardiovasc Electrophysiology, 5(8): 699-710, 1994, Abstract.

Franz "Method and Theory of Monophasic Action Potential Recording", Prog. Cardiovasc Dis, 33(6): 347-368, 1991.

Franz "Progress in Cardiovascular Disease: Monophasic Action Potential Symposium, I. Introduction", Progresses in Cardiovascular Diseases, 33(6): 345-346, 1991.

Fromer et al. "Ultrarapid Subthreshold Stimulation for Termination of Atriventricular Node Reentrant Tachycardia", Journal of the American College Cardiology, 20: 879-883, 1992.

Fu et al. "System Identification of Electrically Coupled Smooth Music Cells: The Passive Electrically Coupled Smooth Muscle Cells: The Passive Electrical Properties", IEEE Transactions on Biomedical Engineering, 38(11): 1130-1140, 1991.

Gill et al. "Refractory Period Extension During Ventricular Pacing at Fibrillatory Pacing Rates", Pacing and Clinical Elctrophysiology, 20(3): 647-653, 1997, Abstract.

Ham et al. "Classification of Cardiac Arrhythmias Using Fuzzy Artmap", IEEE Transactions on Biomedical Engineering, 43(4): 425-429, 1996, Abstract.
Josephson "Clinical Cardiac Electrophysiology: Techniques and Interpretations", Lea & Febiger, 2nd Ed., 2 P., 1991.
Knisley et al. "Effect of Field Stimulation on Cellular Repolarization in Rabbit Myocardium", Circulation Research, 70: 707-715, 1991.
Knisley et al. "Prolgongation and Shortening of Action Potentials by Electrical Shocks in Frog Ventricular Muscle", American Journal of Physiology, 266(6): H2348-H2358, 1994, Abstract.
Koller et al. "Relation Between Repolarization and Refractoriness During Programmed Electrical Stimulation in the Human Right Ventricle", Circulation, 91(9): 2378-2384, 1995, Abstract.
Langberg et al. "Identification of Ventricular Tachycardia with Use of the Morphology of the Endocardial Electrogram", Circulation, 77(6): 1363-1369, 1988.
Lindstrom et al. "Intracellular Calcium Oscillations in a T-Cell Line After Exposure to Extremely-Low-Frequency Magnetic Fields with Variable Frequencies and Flux Densities", Bioelectromagnetics, 16(1): 41-47, 1995, Abstract.
Lubart et al. "Effect of Light on Calcium Transport in Bull Sperm Cells", J. Photochemical Photobiology, 14: 337-341, 1992.
Matheny et al. "Vagus Nerve Stimulation as a Method to Temporarily Slow or Arrest the Heart", Annals of Thoracic Surgery, 63(6): S28-29, 1997, Abstract.
McVeigh et al. "Noninvasive Measurement of Transmural Gradients in Myocardial Strain With MR Imaging", Radiology, 180(3): 677, 679-684, 1991.
Moran et al. "Digoxin-Specific Fab Fragments Impair Renal Function in the Rat", Journal of Pharmacy and Pharmacology, 46(10): 854-856, 1994, Abstract.
Morse et al. "A Guide to Cardiac Pacemakers, Defibrillators and Related Products", Jun. 1991.
Nannini et al. "Muscle Recruitment With Intrafascicular Electrodes",IEEE Transactions on Biomedical Engineering, 38: 769-776, 1991, Abstract.
Pumir et al. "Control of Rotating Waves in Cardiac Muscle: Analysis of the Effect of Electric Fields", Proceedings: Biological Sciences, 257(1349): 129-134, 1994, Abstract.
Ranjan et al. "Electrical Stimulation of Cardiac Myocytes", Annals of Biomedical Engineering, 23(6): 812-821, 1995, Abstract.
Saksena et al. "Prevention of Recurrent Atrial Fibrillation With Chronic Dual-Site Right Atrial Pacing", Journal of the American College of Cardiology, 28(3): 687-694, 1996, Abstract.
Schwartz et al. "Exposure of Frog Hearts to CW or Amplitude-Modified VHF Fields: Selective Efflux of Calcium Ions at 16 Hz", Bioelectromagnetics, 11(4): 349-358, 1990, Abstract.
Shumaik et al. "Oleander Poisoning: Treatment With Digoxin-Specific Fab Antibody Fragments", Annals of Emergency Medicine, 17(7): 732-735, 1988.
Skale et al. "Inhibition of Premature Ventricular Extrastimuli by Subthreshold Conditioning Stimuli", J. Am. Coll. Cardiol., 6: 133-140, 1985, Abstract.
Sweeny et al. "Countershock Strength-Duration Relationship for Myocardial Refractory Period Extension", Academic Emergency Medicine, 2(1): 57-62, 1995, Abstract.
Sweeny et al. "Refractory Interval After Transcardiac Shocks During Ventricular Fibrillation", Circulation, 94(11): 2947-2952, 1996.
Sweeny et al. "Ventricular Refractory Period Extension Caused by Defibrillation Shocks", Circulation, 82(3): 965-972, 1990.
Talit et al. "The Effect of External Cardiac Pacing on Stroke Volume", pace, 13(5): 598-602, 1990, Abstract.
Taniguchi et al. "Inhomogeneity of Cellular Activation Time and Vmax in Normal Myocardial Tissue Under Electrical Field Stimulation", Am. J. Physiol., 267: H694-H705, 1994, Abstract.
Thakor et al. "Effect of Varying Pacing Waveform Shapes on Propagation and Hemodynamics in the Rabbit Heart", The Americal Journal of Cardiology, 79(6A): 36-43, 1997, Abstract.
Verrier et al. "Electrophysiologic Basis for T Wave Alternans as An Index of Vulnerability to Ventricular Fibrillation", Journal of Cardiovascular Electrophysiology, 5(5): 445-461, 1994. Abstract.
Webster Design of Cardiac Pacemakers, IEEE Press, p. xi-xiii, 1995.

Windle et al. "Subthreshold Conditioning Stimuli Prolong Human Ventricular Refractoriness", Am. J. Cardiol., 57(6): 381-386, 1986, Abstract.
Wirtzfeld et al. "Physiological Pacing: Present Status and Future Developments", Pace, 10(Part I): 41-57, 1987. Abstract.
Xue et al. "Neural-Network-Based Adaptive Matched Filtering for QRS Detection", IEEE Transactions on Biomedical Engineering, 39(4): 317-329, 1992, Abstract.
Zipes et al. "Cardiac Electrophysiology—From Cell to Bedside", Saunders Co., 4th Ed., 1990.
Response Dated Jul. 27, 2010 to Communication Pursuant to Article 94(3) EPC of Jan. 27, 2010 From the European Patent Office Re. Application No. 07110023.4.
Response Dated Aug. 1, 2010 to Notification of Reasons of Rejection of Apr. 12, 2010 From the Japanese Patent Office Re.: Application No. 2006-525265.
Response Dated Aug. 2, 2010 to Official Action of Mar. 31, 2010 From the US Patent and Trademark Office Re.: U.S. Appl. No. 10/237,263.
Response Dated Jul. 26, 2010 to Official Action of Mar. 25, 2010 From the US Patent and Trademark Office Re.: U.S. Appl. No. 10/804,560.
Official Action Dated Apr. 16, 2010 From the US Patent and Trademark Office Re.: U.S. Appl. No. 11/566,775.
Response Dated Jan. 5, 2010 to Official Action of Oct. 8, 2009 From the US Patent and Trademark Office Re. U.S. Appl. No. 11/566,775.
Official Action Dated Jun. 8, 2011 From the US Patent and Trademark Office Re. U.S. Appl. No. 11/566,775.
Official Action Dated Oct. 8, 2009 From the US Patent and Trademark Office Re. U.S. Appl. No. 11/566,775.
Official Action Dated Dec. 9, 2010 From the US Patent and Trademark Office Re. U.S. Appl. No. 11/566,775.
Official Action Dated Apr. 16, 2010 From the US Patent and Trademark Office Re. U.S. Appl. No. 11/566,775.
Response Dated Aug. 24, 2010 to the Supplementary European Search Report of Jun. 7, 2010 From the European Patent Office Re. Application No. 04770468.9.
Response Dated Aug. 28, 2011 to Summons to Attend Oral Proceedings Pursuant to Rule 115(1) EPC of Jul. 4, 2011 From the European Patent Office Re.: Application No. 03794043.4.
Summons to Attend Oral Proceedings Pursuant to Rule 115(1) EPC Dated Jul. 4, 2011 From the European Patent Office Re.: Application No. 03794043.4.
Response Dated Aug. 26, 2011 to the Summons to Oral Proceedings of Jul. 4, 2011 From the European Patent Office Re.: Application No. 03794043.4.
Response Dated Sep. 20, 2010 to Official Action of May 21, 2010 From the US Patent and Trademark Office Re. U.S. Appl. No. 10/116,201.
Response Dated Sep. 27, 2010 to Official Action of Apr. 27, 2010 From the US Patent and Trademark Office Re.: U.S. Appl. No. 10/570,576.
Official Action Dated Sep. 27, 2010 From the US Patent and Trademark Office Re.: U.S. Appl. No. 10/804,560.
Response Dated Oct. 13, 2010 to Official Action of Apr. 30, 2010 From the US Patent and Trademark Office Re.: U.S. Appl. No. 11/932,149.
Communication Pursuant to Article 94(3) EPC Dated Oct. 10, 2011 From the European Patent Office Re. Application No. 07110023.4.
European Search Report and the European Search Opinion Dated Jul. 27, 2007 From the European Patent Office Re. Application No. 07110023.4.
Official Action Dated Oct. 5, 2010 From the US Patent and Trademark Office Re.: U.S. Appl. No. 10/039,845.
Response Dated Sep. 30, 2010 to Official Action of Apr. 30, 2010 From the US Patent and Trademark Office Re.: U.S. Appl. No. 11/931,724.
Rsponse Dated Oct. 5, 2010 to Official Action of May 5, 2010 From the US Patent and Trademark Office Re.: U.S. Appl. No. 11/884,389.
San Mauro et al. "Nerves of the Heart: A Comprehensive Review With A Clinical Point of View", Neuroanatomy, 8: 28-31, 2009.
Official Action Dated Oct. 13, 2010 From the US Patent and Trademark Office Re.: U.S. Appl. No. 10/237,263.

Official Action Dated Oct. 13, 2010 From the US Patent and Trademark Office Re.: U.S. Appl. No. 11/919,491.
Response Dated Jul. 13, 2010 to Notice of Reasons for Rejection of Apr. 27, 2010 From the Japanese Patent Office Re.: Application No. 2007-206282.
Official Action Dated Nov. 1, 2011 From the US Patent and Trademark Office Re.: U.S. Appl. No. 10/804,560.
Response Dated Oct. 10, 2011 to Official Action Dated May 11, 2011 From the US Patent and Trademark Office Re.: U.S. Appl. No. 10/804,560.
U.S. Appl. No. 90/008,688, filed Jun. 15, 2007, Ben Haim.
U.S. Appl. No. 90/008,689, filed Jul. 5, 2007, Ben Haim.
U.S. Appl. No. 90/008,707, filed Jun. 7, 2007, Ben Haim.
U.S. Appl. No. 95/000,032, Ben Haim.
Amended Request for Ex Parte Reexamination of US Patent No. 6,317,631 Dated Aug. 20, 2007, U.S. Appl. No. 90/008,689.
Communication Pursuant to Article 94(3) EPC Dated Mar. 2, 2009 From the European Patent Office Re.: Application No. 05853465.2.
Communication Pursuant to Article 94(3) EPC Dated Jan. 28, 2009 From the European Patent Office Re.: Application No. 03794043.4.
Communication Pursuant to Article 94(3) EPC Dated Jan. 29, 2009 From the European Patent Office Re.: Application No. 04106247.2.
Examination Report Dated Jun. 26, 2009 From the Government of India, Patent Office Re.: Application No. 1161/CHENP/2006.
Inter Partes Reexamination Communication of Patent US 6,330,476 Dated Sep. 4, 2007 From the US Patent and Trademark Office Re.: U.S. Appl. No. 95/000,032.
International Preliminary Report on Patentability Dated Dec. 1, 2004 From the International Preliminary Examining Authority Re.: Application No. PCT/IL03/00736.
International Preliminary Report on Patentability Dated Nov. 15, 2007 From the International Bureau of WIPO Re.: Application No. PCT/US2006/017281.
International Preliminary Report on Patentability Dated Jun. 21, 2007 From the International Bureau of WIPO Re.: Application No. Jun. 21, 2007.
International Preliminary Report on Patentability Dated Sep. 27, 2007 From the International Bureau of WIPO Re.: Application No. PCT/IL2006/000345.
International Preliminary Report on Patentability Dated Aug. 30, 2007 From the International Bureau of WIPO Re.: Application No. PCT/IL2006/000204.
Notification of Reasons of Rejection Dated Sep. 29, 2008 From the Japanese Patent Office Re.: Application No. 2004-534013 and Its Translation Into English.
Office Action Dated Nov. 7, 2008 From the State Intellectual Property Office of the People's Republic of China Re.: Application No. 03824661.9 and Its Translation Into English.
Office Action Dated May 8, 2009 From the State Intellectual Property Office of the People's Republic of China Re.: Application No. 03824661.9 and Its Translation Into English.
Office Action Dated Oct. 12, 2004 From the Israeli Patent Office Re.: Application No. 128955.
Office Action Dated Dec. 15, 2008 From the State Intellectual Property Office (SIPO) of the People's Republic of China Re.: Application No. 200480012687.5 and Its Translation Into English.
Official Action Dated Aug. 1, 2007 From the US Patent and Trademark Office Re.: U.S. Appl. No. 90/008,312.
Official Action Dated Mar. 6, 2009 From the US Patent and Trademark Office Re.: U.S. Appl. No. 11/931,889.
Official Action Dated Mar. 6, 2009 From the US Patent and Trademark Office Re.: U.S. Appl. No. 11/932,064.
Official Action Dated Aug. 8, 2007 From the US Patent and Trademark Office Re.: U.S. Appl. No. 10/804,560.
Official Action Dated Sep. 12, 2008 From the US Patent and Trademark Office Re.: U.S. Appl. No. 10/039,845.
Official Action Dated Sep. 13, 2007 From the US Patent and Trademark Office Re.: U.S. Appl. No. 10/237,263.
Official Action Dated Jul. 14, 2008 From the US Patent and Trademark Office Re.: U.S. Appl. No. 10/526,708.
Official Action Dated Jul. 15, 2008 From the US Patent and Trademark Office Re.: U.S. Appl. No. 10/116,201.
Official Action Dated Jul. 18, 2007 From the US Patent and Trademark Office Re.: U.S. Appl. No. 10/039,845.
Official Action Dated Jul. 19, 2007 From the US Patent and Trademark Office Re.: U.S. Appl. No. 10/526,708.
Official Action Dated Jun. 19, 2008 From the US Patent and Trademark Office Re.: U.S. Appl. No. 10/237,263.
Official Action Dated Jun. 23, 2009 From the US Patent and Trademark Office Re.: U.S. Appl. No. 10/549,216.
Official Action Dated Jun. 26, 2008 From the US Patent and Trademark Office Re.: U.S. Appl. No. 11/536,794.
Official Action Dated Mar. 27, 2008 From the US Patent and Trademark Office Re.: U.S. Appl. No. 10/804,560.
Official Action Dated Aug. 31, 2007 From the US Patent and Trademark Office Re.: U.S. Appl. No. 11/536,794.
Response Dated Apr. 20, 2006 to Communication Pursuant of Article 96(2) EPC of Nov. 2, 2005 From the European Patent Office Re.: Application No. 97929478.2.
Request for Ex Parte Reexamination of Patent No. 6,363,279—Notice of Intent to Issue Reexamination Certificate Dated Mar. 18, 2009, U.S. Appl. No. 90/008,688.
Request for Ex Parte Reexamination of Patent No. 6,363,279—Official Action Dated Jun. 20, 2008, U.S. Appl. No. 90/008,688.
Request for Ex Parte Reexamination of Patent No. 6,363,279—Order Granting Request Dated Nov. 5, 2007, U.S. Appl. No. 90/008,688.
Request for Ex Parte Reexamination of Patent No. 6,363,279 Dated Jun. 8, 2007, U.S. Appl. No. 90/008,688.
Request for Ex Parte Reexamination of Patent No. 6,363,279—IDS Submitted Dec. 31, 2007, U.S. Appl. No. 90/008,688.
Request for Ex Parte Reexamination of Patent No. 6,363,279, Response to Official Action Dated Jun. 20, 2008 Submitted Aug. 20, 2008, U.S. Appl. No. 90/008,688.
Request for Ex Parte Reexamination of US Patent No. 6,236,887—IDS Submitted Oct. 17, 2007, U.S. Appl. No. 90/008,707.
Request for Ex Parte Reexamination of US Patent No. 6,236,887—IDS Submitted Sep. 29, 2008, U.S. Appl. No. 90/008,707.
Request for Ex Parte Reexamination of US Patent No. 6,236,887—Notice of Intent to Issue Ex Parte Examination Certificate Dated Mar. 19, 2009, U.S. Appl. No. 90/008,707.
Request for Ex Parte Reexamination of US Patent No. 6,236,887—Official Action and IDS Considered Dated Jun. 20, 2008, U.S. Appl. No. 90/008,707.
Request for Ex Parte Reexamination of US Patent No. 6,236,887—Official Action Granting Request for Ex Parte Examination Dated Aug. 17, 2007, U.S. Appl. No. 90/008,707.
Request for Ex Parte Reexamination of US Patent No. 6,236,887 Dated Jun. 13, 2007, U.S. Appl. No. 90/008,707.
Request for Ex Parte Reexamination of US Patent No. 6,298,268—Certificate of Reexamination Issued Mar. 7, 2006, U.S. Appl. No. 90/006,788.
Request for Ex Parte Reexamination of US Patent No. 6,298,268—IDS Considered Feb. 22, 2005, U.S. Appl. No. 90/006,788.
Request for Ex Parte Reexamination of US Patent No. 6,298,268—Notice of Intent to Issue Certificate of Reexamination Dated Mar. 29, 2005, U.S. Appl. No. 90/006,788.
Request for Ex Parte Reexamination of US Patent No. 6,298,268 Dated Oct. 10, 2003, U.S. Appl. No. 90/006,788.
Request for Ex Parte Reexamination of US Patent No. 6,298,268 Order Granting Request for Ex Parte Reexamination Dated Dec. 19, 2003, U.S. Appl. No. 90/006,788.
Request for Ex Parte Reexamination of US Patent No. 6,317,631—Amendment in Response to Official Action Dated Jun. 20, 2008, Filed Aug. 20, 2008, U.S. Appl. No. 90/008,689.
Request for Ex Parte Reexamination of US Patent No. 6,317,631—IDS Dated Dec. 31, 2007, U.S. Appl. No. 90/008,689.
Request for Ex Parte Reexamination of US Patent No. 6,317,631—IDS Dated Sep. 26, 2008, U.S. Appl. No. 90/008,689.
Request for Ex Parte Reexamination of US Patent No. 6,317,631—Notice of Intent to Issue Certificate of Reexamination Dated Mar. 18, 2009, U.S. Appl. No. 90/008,689.
Request for Ex Parte Reexamination of US Patent No. 6,317,631—Official Action Dated Jun. 20, 2008, U.S. Appl. No. 90/008,689.

Request for Ex Parte Reexamination of US Patent No. 6,317,631—Order Granting Reexamination Dated Nov. 5, 2007, U.S. Appl. No. 90/008,689.
Request for Ex Parte Reexamination of US Patent No. 6,317,631—IDS Dated Jun. 8, 2007, U.S. Appl. No. 90/008,689.
Request for Ex Parte Reexamination of US Patent No. 6,330,476—IDS Dated May 31, 2006.
Request for Ex Parte Reexamination of US Patent No. 6,330,476—Comments by 3rd Party Requestor, Response Thereto and Official Action Issued Jul. 16, 2008, U.S. Appl. No. 95/000,032.
Request for Ex Parte Reexamination of US Patent No. 6,330,476—Communication of Right to Appeal dated Jul. 16, 2008, U.S. Appl. No. 95/000,032.
Request for Ex Parte Reexamination of US Patent No. 6,330,476—IDS Filed May 4, 2007, U.S. Appl. No. 95/000,032.
Request for Ex Parte Reexamination of US Patent No. 6,330,476—Official Action by USPTO Issued Mar. 23, 2004, U.S. Appl. No. 95/000,032.
Request for Ex Parte Reexamination of US Patent No. 6,330,476—Order Granting Request for Reexamination Dated Mar. 23, 2004, U.S. Appl. No. 95/000,032.
Request for Ex Parte Reexamination of US Patent No. 6,330,476 Dated Dec. 31, 2003, U.S. Appl. No. 95/000,032.
Request for Ex Parte Reexamination of US Patent No. 6,463,324—Amendment in Response to Official Action Dated Aug. 1, 2007 Filed Oct. 1, 2007, U.S. Appl. No. 90/008,312.
Request for Ex Parte Reexamination of US Patent No. 6,463,324—Certificate of Reexamination Dated Apr. 29, 2008, U.S. Appl. No. 90/008,312.
Request for Ex Parte Reexamination of US Patent No. 6,463,324—Official Action—Notice of Intent to Reexamine Dated Jan. 24, 2008, U.S. Appl. No. 90/008,312.
Request for Ex Parte Reexamination of US Patent No. 6,463,324—Official Action Dated Aug. 1, 2007, U.S. Appl. No. 90/008,312.
Request for Ex Parte Reexamination of US Patent No. 6,463,324—Official Action, Interview Summary and References Considered Dated Nov. 6, 2007, U.S. Appl. No. 90/008,312.
Request for Ex Parte Reexamination of US Patent No. 6,463,324 Dated Nov. 1, 2006, U.S. Appl. No. 90/008,312.
Response Dated Jan. 17, 2008 to Official Action of Jul. 18, 2007 From the US Patent and Trademark Office Re.: U.S. Appl. No. 10/039,845.
Response Dated Oct. 1, 2007 to Official Action of Aug. 1, 2007 From the US Patent and Trademark Office Re.: U.S. Appl. No. 90/008,312.
Response Dated Sep. 1, 2004 to Communication Pursuant to Article 96(2) EPC of Mar. 2, 2004 From the European Patent Office Re.: Application No. 97929478.2.
Response Dated Apr. 3, 2008 to Official Action of Jan. 3, 2008 From the US Patent and Trademark Office Re.: U.S. Appl. No. 10/116,201.
Response Dated May 4, 2009 to Official Action of Nov. 3, 2008 From the US Patent and Trademark Office Re.: U.S. Appl. No. 10/116,201.
Response Dated Oct. 4, 2007 to Official Action of Sep. 4, 2007 From the US Patent and Trademark Office Re.: U.S. Appl. No. 95/000,032.
Response Dated May 7, 2007 to Examination Report of Mar. 2, 2007 From the Government of India, Patent Office Re.: Application No. 533/CHENP/2005.
Response Dated Aug. 20, 2008 to Official Action of Jun. 20, 2008 From the US Patent and Trademark Office Re.: U.S. Appl. No. 90/008,689.
Response Dated May 21, 2008 to Office Action of Dec. 11, 2007 From the Japanese Patent Office Re.: Application No. 09-525055.
Response Dated Dec. 24, 2006 to Office Action of Jul. 18, 2006 From the Japanese Patent Office Re.: Application No. 10-513446.
Response Dated Dec. 25, 2006 to Notice of Reasons for Rejection of Jul. 18, 2006 From the Japanese Patent Office Re.: Application No. 09-529637.
Response Dated Jan. 25, 2007 to Examination Report of Jul. 7, 2006 From the Government of India, Patent Office Re.: Application No. 533/CHENP/2005.
Summons to Attend Oral Proceedings Pursuant to Rule 115(1) EPC Dated Dec. 22, 2008 From the European Patent Office Re.: Application No. 97929480.8.

Supplementary European Search Report and the European Search Opinion Dated Nov. 28, 2008 From the European Patent Office Re.: Application No. 05853465.2.
Translation of Decision of Rejection Dated Apr. 22, 2009 From the Japanese Patent Office Re.: Application No. 2004-534013.
Translation of Notice of Reasons for Rejection Dated Jul. 18, 2006 From the Japanese Patent Office Re.: Application No. 9-529637.
Translation of Office Action Dated Sep. 12, 2008 From the State Intellectual Property Office of the People's Republic of China Re.: Application No. 200480032636.9.
Antoni, H. et al., "Polarization Effects of Sinusoidal 50-Cycle Alternating Current on Membrane Potential of Mammalian Cardiac Fibres"; Pflugers Arch.; 1970; 314; pp. 274-291.
Babsky Ye. B. et al., "Physiology of Man"; M. Medicine; 1972; pp. 350-385.
Saveliev, V.S. et al, "Guidebook on Clinical Endoscopy"; M. Medicine; 1985; pp. 21, 35 and translation of extracts.
Zhou, X. et al, "Prevention of Action Potentials During Extracellular Electrical Stimulation of Long Duration"; J.Cardiovasc. Electrophysiol.; 1997; vol. 8; pp. 779-789.
Devedeux, D. et al, "Uterine electromyography: a critical review"; Am. J. Obstet. Gynecol.; 1993; vol. 169(6); pp. 1636-1653; abstract of article.
Van Ripper, D. et al, "Electrical Field Stimulation—Mediated Relaxation of a Rabbit Middle Cerebral Artery"; Circulation Research; 1992; vol. 70; pp. 1104-1112.
Shuba, M.F. et al; "Physiology of vessel smooth muscles"; Kiev; Naukova Dumka; 1988; pp. 11-15; 142 and translation of extracts.
Pokrovsky, V.M. et al; "Physiology of Man"; Moscow; Medicine; 1997; vol. 1; pp. 82-83, 94; vol. 2; pp. 42, 54 and translation of extracts.
Shmit, R. et al; "Physiology of Man"; Moscow; Mir; 1996; vol. 1; pp. 78 and translation of extract.
Bogolyubov, V.M. et al; "Balneology and Physiotherapy"; M. Medicine; 1985; v. 2; pp. 420.
Gomis, A. et al.; "Oscillatory Patterns of Electrical Activity in Mouse Pancreatic Islets of Langerhans Recorded in Vivo;" Jul. 1996; Pflügers Arch.—Eur. J. Physiol.; vol. 432, No. 3; pp. 510-515.
Jaremko, J. et al.; "Advances Toward the Implantable Artificial Pancreas for Treatment of Diabetes;" Mar. 1998; Diabetes Care; vol. 21, No. 3; pp. 444-450.
Magnus, G. et al.; "Model of β-Cell Mitochondrial Calcium Handling and Electrical Activity. II. Mitochondrial Variables;" Apr. 1998; American Journal of Physiology; vol. 274; Cell Physiol. 43; pp. C1174-C1184.
Nadal, A. et al.; "Homologous and Heterologous Asynchronicity Between Identified α-, β- and δ-Cells Within Intact Islets of Langerhans in the Mouse;" May 1999; Journal of Physiology vol. 517, Pt. 1; pp. 85-93.
Soria, B. et al.: "Cytosolic Calcium Oscillations and Insulin Release in Pancreatic Islets of Langerhans;" Feb. 1998; Diabetes & Metabolism (Paris;) vol. 24, No. 1; pp. 37-40.
Serre, V. et al.; "Exendin-(9-39) Is an Inverse Agonist of the Murine Glucagon-Like Peptide-1 Receptor: Implications for Basal Intracellular Cyclic Adenosine 3',5'—Monophosphate Levels and B-Cell Glucose Competence;" Nov. 1998; pp. 4448-4454; Endocrinology; vol. 139; No. 11.
Valdeolmillos, M. et al.; "In Vivo Synchronous Membrane Potential Oscillation in Mouse Pancreatic B-Cells: Lack of Co-ordination Between Islets;" 1996; pp. 9-18; Journal of physiology; vol. 493; No. 1.
Schirra, J. et al.; "Exendin(9-39)amide Is an Antagonist of Glucagon-Like Peptide-1 (7-36) amide in Humans;" Apr. 1, 1998; pp. 1421-1430; Journal of Clinical Investigation; vol. 101; No. 7.
Best and Taylor's Physiological Basis of Medical Practice; edited by West, J.B.; 12th Edition; Chaper 50; "The Endocrine Pancreas;" pp. 754-769; Williams & Wilkins, 1991.
Yonemura, Y. et al.; "Amelioration of Diabetes Mellitus in Partially Depancreatized Rats by Poly(ADP-Ribose) Synthetase Inhibitors. Evidence of Islet B-Cell Regeneration;" Apr. 1984; Diabetes; vol. 33; No. 4; pp. 401-404.

Holst, J. J. et al.; "Nervous Control of Pancreatic Endocrine Secretion in Pigs;" Jan. 1981; Acta Physiologica Scandinavica; vol. 111; pp. 1-7; XP000980527.

Rivera, V. M. et al.; "Regulation of Protein Secretion Through Controlled Aggregation in the Endoplasmic Reticulum;" Feb. 4, 2000; pp. 826-830; Science; vol. 287.

Davis, S. N. et al.; "Insulin, Oral Hypoglycemic Agents, and the Pharmacology of the Endocrine Pancreas;" The Pharmacological Basis of Therapeutics; Chapter 60; pp. 1487-1499; pp. 1507-1510; edited by Hardman, J. G. et al., 2001.

Bergsten, P. et al.; "Synchronous Oscillations of Cytoplasmic Ca2+ and Insulin Release in Glucose-Stimulated Pancreatic Islets;" Mar. 1994; pp. 8749-8753; The Journal of Biological Chemistry; vol. 269; No. 12.

Palti, Y. et al.; "Islets of Langerhans Generate Wavelike Electric Activity Modulated by Glucose Concentration;" May 1996; pp. 595-601; Diabetes; vol. 45.

Kuffler, S. W. et al.; "Release of Chemical Transmitters;" Chapter 10; pp. 241-261; From Neuron to Brain, a Cellular Approach to the Function of the Nervous System; Second Edition; Sinauer Associates Inc. Publishers; Sunderland, Massachusetts, 1992.

Singh, J. et al.; "Effects of Islet Hormones on Nerve-Mediated and Acetylcholine-Evoked Secretory Responses in the Isolated Pancreas of Normal and Diabetic Rats;" Mar. 1998; pp. 627-634; International Journal of Molecular Medicine; vol. 1; No. 3; XP000980499.

Hinke, S. A. et al.; "Dipeptidyl Peptidase IV (DPIV/CD26) Degradation of Glucagon, Characterization of Glucagon Degradation Products and DPIV-Resistant Analogs;" Feb. 11, 2000; pp. 3827-3834; The Journal of Biological Chemistry 2000; vol. 275; No. 6.

Wright, L. M. et al.; "Stracture of Fab hGR-2 F6, a Competitive Antagonist of the Glucagon Receptor;" May 2000; pp. 73-580; Acta Crystallographica Section D Biological Crystallography; vol. 56 (pt 1).

Meurer, J. A. et al.; "Properties of Native and In Vitro Glycosylated Forms of the Glucagon-Like Peptide-1 Receptor Antagonist Exendin(9-39);" Jun. 1999; pp. 716-724; Metabolism; vol. 48; No. 6.

Wang, F. et al.; "Islet Amyloid Polypeptide Tonally Inhibits –, =, and -Cell Secretion in Isolated Rat Pancreatic Islets;" Jan. 1999; pp. E19-E24; American Journal of Physiology; vol. 276 (1 pt 1), 1999.

Ohinata, K. et al.; "Proadrenomedullin N-Terminal 20 Peptide (PAMP) Elevates Blood Glucose Levels Via Bombesin Receptor in Mice;" May 12, 2000; pp. 207-211; FEBS Letters; vol. 473; No. 2.

Shah, P. et al.; "Impact of Lack of Suppression of Glucagon on Glucose Tolerance in Humans; Aug. 1999; pp. E283-E290; American Journal of Physiology; vol. 277 (2 pt 1).

Liu, S. et al.; "2-Pyridylthioureas: Novel Nonpeptide Somatostatin Agonists with SST4 Selectivity;" Apr. 1999; pp. 255-263; Current Pharmaceutical Design; vol. 5; No. 4.

Bouaziz, A. et al.; "Direct Electrical Stimulation of Insulin Secretion by Intact Murine Islets of Langerhans Through the Culture Support;" 1998; pp. 171-184; Electro- and Magnetobiology; vol. 17; No. 2.

Misler, S. et al.; "Electrophysiology of Stimulus-Secretion Coupling in Human b-Cells;" Oct. 1992; pp. 1221-1228; Diabetes; vol. 41.

Gold, G. et al.; Evidence that Glucose "Marks" b Cells Resulting in Preferential Release of Newly Synthesized Insulin; Oct. 1, 1982; pp. 56-58; Science; vol. 218.

Kurose, T. et al.; "Glucagon, Insulin and Somatostatin Secretion in Response to Sympathetic Neural Activation in Streptozotocin-Induced Diabetic Rats. A Study with the Isolated Perfused Rat Pancreas In Vitro;" 1992; pp. 1035-1041; Diabetologia; vol. 35.

Holst, J. J. et al.; "Nervous Control of Pancreatic Endocrine Secretions in Pigs;" Jan. 1981; pp. 9-14; Acta Physiologica Scandinavical; vol. 111; XP000980528.

Park, H. S. et al.; "Significant Cholinergic Role in Secretin-Stimulated Exocrine Secretion in Isolated Rat Pancreas;" Feb. 1998; pp. G413-G418; American Journal of Physiology; vol. 274; No. 2; Pt. 1, XP002157834.

Communication Pursuant to Article 94(3) EPC Dated Aug. 30, 2012 From the European Patent Office Re. Application No. 07110023.4.

Supplementary European Search Report and the European Search Opinion Dated Sep. 25, 2012 From the European Patent Office Re.: Application No. 06711186.4.

* cited by examiner

BLOOD GLUCOSE LEVEL CONTROL

RELATED APPLICATIONS

This application is Divisional of U.S. patent application Ser. No. 09/914,889 filed Sep. 4, 2001 which is a U.S. national phase filing of PCT application No. PCT/IL00/00132, filed Mar. 5, 2000. This application claims the benefit under 119(e) of U.S. provisional application 60/123,523, filed Mar. 5, 1999, the disclosure of which is incorporated herein by reference.

FIELD OF THE INVENTION

The present invention is related to the field of controlling blood serum glucose levels, especially by application of electric fields to a pancreas, to control insulin output.

BACKGROUND OF THE INVENTION

Control of insulin secretion is very important, as there are many living diabetes patients whose pancreas is not operating correctly. In some type of diabetes, the total level of insulin is reduced below that required to maintain normal blood glucose levels. In others, the required insulin is generated, but only at an unacceptable delay after the increase in blood glucose levels. In others, the body is, for some reason, resistant to the effects of insulin.

Although continuous (e.g., avoiding dangerous spikes and dips) of blood glucose level is desirable, it cannot currently be achieved in some patients.

The insulin secretion process operates as follows: glucose levels in the blood are coupled to depolarization rates of beta islet cells in the Pancreas. It is postulated that when there is a higher glucose level, a higher ratio of ATP/ADP is available in the beta cell and this closes potassium channels, causing a depolarization of the beta cell. When a beta cell depolarizes, the level of calcium in the cell goes up and this elevated calcium level causes the conversion of pro-insulin to insulin and causes secretion of insulin from the cell.

The beta cells are arranged in islets, within a reasonable range of blood glucose levels, an action potential is propagated in the islet. Generally, the electrical activity of a beta cell in an islet is in the form of bursts, each burst comprises a large number of small action potentials.

In PCT publication WO 99/03533, the disclosure of which is incorporated here by reference, it was suggested to reduce the output of a pancreas using a non-excitatory electric field.

PCT publication WO 98/57701 to Medtronic, the disclosure of which is incorporated herein by reference, suggests providing a stimulating electric pulse to an islet, causing an early initiation of a burst and thus, increasing the frequency of the bursts and increasing insulin secretion.

The above PCT publication to Medtronic suggests providing a stimulating (e.g., above stimulation threshold) pulse during a burst, thereby stopping the burst and reducing insulin secretion. This publication also suggests stimulating different parts of the pancreas in sequence, thereby allowing unstimulated parts to rest.

However, one limitation of the methods described in the Medtronic PCT publication is that increasing the burst frequency increases the level of intra-cellular calcium in the beta cells over a long period of time, without the level being allowed to go down, during intra-burst intervals. This increase may cause various cell death mechanisms to be activated and/or otherwise upset the normal balance of the beta cell, eventually killing the cell. In addition, such high calcium levels may cause hyper-polarization of beta cells, thereby reducing insulin secretion and preventing propagation of action potentials. To date, no working electrical pancreatic control device is known.

SUMMARY OF THE INVENTION

An aspect of one preferred embodiment of the invention relates to a method of increasing insulin secretion, while avoiding unacceptable calcium level profiles. In a preferred embodiment of the invention, insulin output is increased by extending a burst duration, while maintaining a suitably lengthy interval between bursts, thus allowing calcium levels to decay during the interval. Alternatively or additionally, insulin output is increased by increasing the effectiveness of calcium inflow during a burst, possibly without changing the burst frequency and/or duty cycle. Alternatively, in both methods, the burst frequency may be reduced and/or the interval increased, while allowing higher insulin output levels or maintaining same output levels.

In a preferred embodiment of the invention, the effects on insulin secretion are provided by applying a non-excitatory pulse to at least part of the pancreas. As used herein the term non-excitatory is used to describe a pulse that does not generate a new action potential, but may modify an existing or future potential. This behavior may be a result of the pulse, amplitude, frequency or pulse envelope, and generally also depends on the timing of the pulse application. It is noted that a single pulse may have excitatory and non-excitatory parts. For example a 100 ms pacing pulse, may cease to have a pacing effect after 20 ms and have real non-excitatory effects after 40 ms.

The pulse may be synchronized to the local electrical activity, for example, to bursts or to individual action potentials. Alternatively or additionally, the pulse may be synchronized to the cycle of changes in insulin level in the blood (typically a 12 minute cycle in healthy humans). Alternatively, the pulse may be unsynchronized to local or global pancreatic electrical activity. Alternatively, the applied pulse may cause synchronization of a plurality of islets in the pancreas, for example by initiating a burst. A two part pulse may be provided, one part to synchronize and one part to provide the non-excitatory activity of the pulse. Although the term "pulse" is used, it is noted that the applied electric field may have a duration longer than an action potential or even longer than a burst.

An aspect of some preferred embodiments of the invention relates to reducing calcium levels in beta islet cells. In a preferred embodiment of the invention, the levels are reduced by providing an oral drug. Alternatively, the levels are reduced by increasing the interval between bursts. The intervals may be increased, for example, by suppressing bursts of action potentials, for example using excitatory or non-excitatory pulses. Alternatively, an electro-physiological drug is provided for that purpose. For example, Procainamide HCL and Quinidine sulfate are Na channel antagonists, Minoxidil and Pinacidil are K channel activators, and Amiloride HCL is an Na channel and epithelial antagonist. Other suitable pharmaceuticals are known in the art, for example as described in the RBI Handbook of Receptor Classification, and available from RBI inc. This reduction in calcium levels may be performed to reduce the responsiveness of the pancreas to glucose levels in the blood. Alternatively or additionally, this reduction is used to offset negative side effects of drugs or other treatment methods and/or to enforce a rest of at least a part of the pancreas. Alternatively or additionally, this reduction may be offset by increasing the effectiveness of insulin secretion.

An aspect of some preferred embodiments of the invention relates to pacing at least a portion of the pancreas and, at a delay after the pacing, applying a non-excitatory pulse. The non-excitatory pulse may be provided to enhance or suppress insulin secretion or for other reasons. In a preferred embodiment of the invention, the pacing pulse provides a synchronization so that the non-excitatory pulse reaches a plurality of cells at substantially a same phase of their action potentials. A further pulse, stimulating or non-excitatory may then be provided based on the expected effect of the non-excitatory pulse on the action potential.

An aspect of some preferred embodiments of the invention relates to simultaneously providing pharmaceuticals and electrical control of a pancreas. In a preferred embodiment of the invention, the electrical control counteracts negative effects of the pharmaceuticals. Alternatively or additionally, the pharmaceutical counteracts negative effects of the electrical control. Alternatively or additionally, the electrical control and the pharmaceutical complement each other, for example, the pharmaceutical affecting the insulin production mechanisms and the electrical control affecting the insulin secretion mechanism. The electrical control and/or the pharmaceutical control may be used to control various facets of the endocrinic pancreatic activity, including one or more of: glucose level sensing, insulin production, insulin secretion, cellular regeneration, healing and training mechanisms and/or action potential propagation. In a preferred embodiment of the invention, electrical and/or pharmaceutical mechanisms are used to replace or support pancreatic mechanisms that do not work well, for example, to replace feedback mechanisms that turn off insulin production when a desired blood glucose level is achieved. The pharmaceuticals that interact with the pancreatic controller may be provided for affecting the pancreas. Alternatively, they may be for other parts of the body, for example for the nervous system or the cardiovascular system.

An aspect of some preferred embodiments of the invention relates to activating pancreatic cells in various activation profiles, for example to achieve training, regeneration, healing and/or optimal utilization. In a preferred embodiment of the invention, such activating can include one or more of excitatory pulses, non-excitatory pulses and application of pharmaceuticals and/or glucose. It is expected that diseased cells cannot cope with normal loads and will degenerate if such loads are applied. However, by providing sub-normal loads, these cells can continue working and possibly heal after a while using self healing mechanisms. In particular, it is expected that certain diseased cells, when stimulated at at least a minimal activation level, will heal, rather than degenerate. Alternatively or additionally, it is expected that by stressing cells by a certain amount, compensation mechanisms, such as increase in cell size, response speed and profile to glucose levels, cell effectiveness and/or cell numbers, will operate, thereby causing an increase in insulin production capability, insulin response time and/or other desirable pancreatic parameters. The appropriate activation profiles may need to be determined on a patient by patient basis. Possibly, different activation profiles are tested on one part of the pancreas, and if they work as desired, are applied to other parts of the pancreas. These other parts of the pancreas may be suppressed during the testing, to prevent over stressing thereof. Alternatively, they may be maintained at what is deemed to be a "safe" level of activity, for example by electrical control or by pharmaceutical or insulin control.

An aspect of some preferred embodiments of the invention relates to electrically affecting and preferably controlling insulin generation, alternatively or additionally to affecting insulin secretion. In a preferred embodiment of the invention, insulin production is enhanced by "milking" insulin out of beta cells so that their supplies of insulin are always under par. Alternatively or additionally, by under-milking such cells (e.g., prevention of secretion), insulin production is decreased. In some patients opposite effects may occur— over milking will cause a reduction in insulin production and/or under-milking will increase insulin production. Alternatively, insulin production is suppressed by preventing a cell from secreting insulin (e.g., by preventing depolarization), thereby causing large amount of insulin to stay in the cell, and possibly, prevent further production of insulin. Such mechanisms for stopping the production of insulin have been detected in pancreatic cells.

In a preferred embodiment of the invention, by causing a cell to store a large amount of insulin, a faster response time can be achieved, when large amounts of insulin are required, for example to combat hyperglycemia. The cells can then be systemically depolarized to yield their stores of insulin. Possibly, a plurality of pancreatic cells (the same or different ones at different times) are periodically set aside to serve as insulin burst providers.

Alternatively or additionally, suppression of insulin output is used during medical procedures, to prevent hypoglycemia. Alternatively or additionally, suppression or enhancement of insulin output is used to overwork pancreatic tumor cells, so they die from over production or from over-storage of insulin. In some cases, the overworking of cells caused by cycling demand may be used as a form of stress to weaken cells, and in combination with another stress source, kill the cells. Alternatively or additionally, suppression of insulin output is used to reduce the activity of an implanted pancreas or pancreatic portion, to assist in its getting over the shock of transplantation.

An aspect of some preferred embodiments of the invention relates to controlling the propagation of action potentials and/or other parameters of action potentials in islet cells, alternatively or additionally to controlling parameters of burst activity. In a preferred embodiment of the invention, a pulse, preferably synchronized to individual action potentials in an islet, is used to control the action potential, for example to increase or decrease its plateau duration. Alternatively or additionally, a reduction in action potential frequency towards the end of a burst is counteracted, for example by pacing the cells to have a desired frequency or to be more excitable.

In a preferred embodiment of the invention, action potential propagation is controlled, for example enhanced or blocked, by selectively sensitizing or desensitizing the beta cells in an islet, using chemical and/or electrical therapy. Enhancement of action potential may be useful for increasing insulin production rates, especially if the glucose sending mechanism in some cells are damaged. Suppression of action potential propagation is useful for preventing insulin production and/or enforcing rest.

An aspect of some preferred embodiments of the invention relates to indirectly affecting the pancreatic activity by changing pancreatic response parameters, such as response time to increases in glucose level and response gain to increases in glucose level. Thus, for example, a non-responsive pancreas can be sensitized, so that even small changes in glucose level will cause an outflow of insulin. Alternatively, a weak or over-responsive pancreas can be desensitized, so that it isn't required to generate (large amounts of) insulin for every small fluctuation in blood glucose level. It is noted that the two treatments can be simultaneously applied to different parts of a single pancreas.

An aspect of some preferred embodiments of the invention relates to synchronizing the activities of different parts of the pancreas. Such synchronization may take the form of all the different parts being activated together. Alternatively, the synchronization comprises activating one part (or allowing it be become active) while suppressing other parts of the pancreas (or allowing them to remain inactive). In a preferred embodiment of the invention, the synchronization is applied to enforce rest on different parts of the pancreas. Alternatively or additionally, the synchronization is provided to selectively activate fast-responding parts of the pancreas or slow responding parts of the pancreas.

In a preferred embodiment of the invention, synchronization between islets or within islets is enhanced by providing pharmaceuticals, for example Connexin, to reduce gap resistance. Such pharmaceuticals may be administered, for example, orally, systemically via the blood locally or locally, for example via the bile duct. In a preferred embodiment of the invention, such pharmaceuticals are provided by genetically altering the cells in the pancreas, for example using genetic engineering methods.

An aspect of some preferred embodiments of the invention relates to implanting electrodes (and/or sensors) in the pancreas. In a preferred embodiment of the invention, the electrodes are provided via the bile duct. Possibly, a controller, attached to the electrode is also provided via the bile duct. In a preferred embodiment of the invention, the implantation procedure does not require general anesthesia and is applied using an endoscope. Alternatively, the electrodes are provided through the intestines. Possibly, also the device which controls the electrification of the electrodes is provided through the intestines. In a preferred embodiment of the invention, the device remains in the intestines, possibly in a folded out portion of the intestines, while the electrodes poke out through the intestines and into the vicinity or the body of the pancreas. Alternatively, the electrodes may be provided through blood vessels, for example the portal vein. In a preferred embodiment of the invention, the electrodes are elongated electrodes with a plurality of dependent or independent contact points along the electrodes. The electrodes may be straight or curved. In a preferred embodiment of the invention, the electrodes are poked into the pancreas in a curved manner, for example being guided by the endoscope, so that the electrodes cover a desired surface or volume of the pancreas. The exact coverage may be determined by imaging, or by the detection of the electric field emitted by the electrodes, during a post implantation calibration step.

An aspect of some preferred embodiments of the invention relates to a pancreatic controller adapted to perform one or more of the above methods. In a preferred embodiment of the invention, the controller is implanted inside the body. An exemplary controller includes one or more electrodes, a power source for electrifying the electrodes and control circuitry for controlling the electrification. Preferably, a glucose or other sensor is provided for feedback control.

There is thus provided in accordance with a preferred embodiment of the invention, a pancreatic controller, comprising:

a glucose sensor, for sensing a level of glucose or insulin in a body serum;

at least one electrode, for electrifying an insulin producing cell or group of cells;

a power source for electrifying said at least one electrode with a pulse that does not initiate an action potential in said cell and has an effect of increasing insulin secretion; and a controller which receives the sensed level and controls said power source to electrify said at least one electrode to have a desired effect on said level. Preferably, said insulin producing cell is contiguous with a pancreas and wherein said electrode is adapted for being placed adjacent said pancreas. Alternatively or additionally, said controller comprises a casing suitable for long term implantation inside the body. Alternatively or additionally, said electrode is adapted for long term contact with bile fluids. Alternatively or additionally, the apparatus comprises an electrical activity sensor for sensing electrical activity of said cell and wherein said power source electrifies said electrode at a frequency higher than a sensed depolarization frequency of said cell, thereby causing said cell to depolarize at the higher frequency.

In a preferred embodiment of the invention, said pulse is designed to extend a plateau duration of an action potential of said cell, thereby allowing more calcium inform into the cell. Preferably, said pulse is deigned to reduce an action potential frequency of said cell, while not reducing insulin secretion from said cell.

In a preferred embodiment of the invention, said pulse is designed to extend a duration of a burst activity of said cell.

In a preferred embodiment of the invention, said pulse has an amplitude sufficient to recruit non-participating insulin secreting cells of said group of cells.

In a preferred embodiment of the invention, the apparatus comprises at least a second electrode adjacent for electrifying a second cell of group of insulin secreting cells, wherein said controller electrifies said second electrode with a second pulse different from said first electrode. Preferably, said second pulse is deigned to suppress insulin secretion. Preferably, said controller is programmed to electrify said second electrode at a later time to forcefully secrete said insulin whose secretion is suppressed earlier. Alternatively, said second pulse is designed to hyper-polarize said second cells.

In a preferred embodiment of the invention, said controller electrifies said at least one electrode with a pacing pulse having a sufficient amplitude to force a significant portion of said cells to depolarize, thus aligning the cells' action potentials with respect to the non-excitatory pulse electrification.

In a preferred embodiment of the invention, said controller synchronizes the electrification of said electrode to a burst activity of said cell.

In a preferred embodiment of the invention, said controller synchronizes the electrification of said electrode to an individual action potential of said cell.

In a preferred embodiment of the invention, said controller does not synchronizes the electrification of said electrode to electrical activity of said cell.

In a preferred embodiment of the invention, said controller does not apply said pulse at every action potential of said cell.

In a preferred embodiment of the invention, said controller does not apply said pulse at every burst activity of said cell.

In a preferred embodiment of the invention, said pulse has a duration of less than a single action potential of said cell. Preferably, said pulse has a duration of less than a plateau duration of said cell.

In a preferred embodiment of the invention, said pulse has a duration of longer than a single action potential of said cell.

In a preferred embodiment of the invention, said pulse has a duration of longer than a burst activity duration of said cell.

In a preferred embodiment of the invention, said controller determines said electrification in response to a pharmaceutical treatment applied to the cell. Preferably, said pharmaceutical treatment comprises a pancreatic treatment. Alternatively or additionally, said controller applies said pulse to counteract adverse effects of said pharmaceutical treatment.

In a preferred embodiment of the invention, said controller applies said pulse to synergistically interact with said pharmaceutical treatment. Alternatively, said controller applies said pulse to counteract adverse effects of pacing stimulation of said cell.

In a preferred embodiment of the invention, said apparatus comprises an alert generator. Preferably, said controller activates said alert generator if said glucose level is below a threshold. Alternatively or additionally, said controller activates said alert generator if said glucose level is above a threshold.

There is also provided in accordance with a preferred embodiment of the invention, a method of controlling insulin secretion, comprising:

providing an electrode to at least a part of a pancreas;

applying a non-excitatory pulse to the at least part of a pancreas, which pulse increases secretion of insulin. Preferably, the method comprises applying an excitatory pulse in association with said non-excitatory pulse. Alternatively or additionally, the method comprises applying a secretion reducing non-excitatory in association with said non-excitatory pulse.

In a preferred embodiment of the invention, the method comprises applying a plurality of pulses in a sequence designed to achieve a desired effect on said at least a part of a pancreas.

BRIEF DESCRIPTION OF THE DRAWINGS

Particular embodiments of the invention will be described with reference to the following description of preferred embodiments in conjunction with the figures, wherein identical structures, elements or parts which appear in more than one figure are preferably labeled with a same or similar number in all the figures in which they appear, in which.

DETAILED DESCRIPTION OF PREFERRED EMBODIMENTS

Overview

Figure 1:
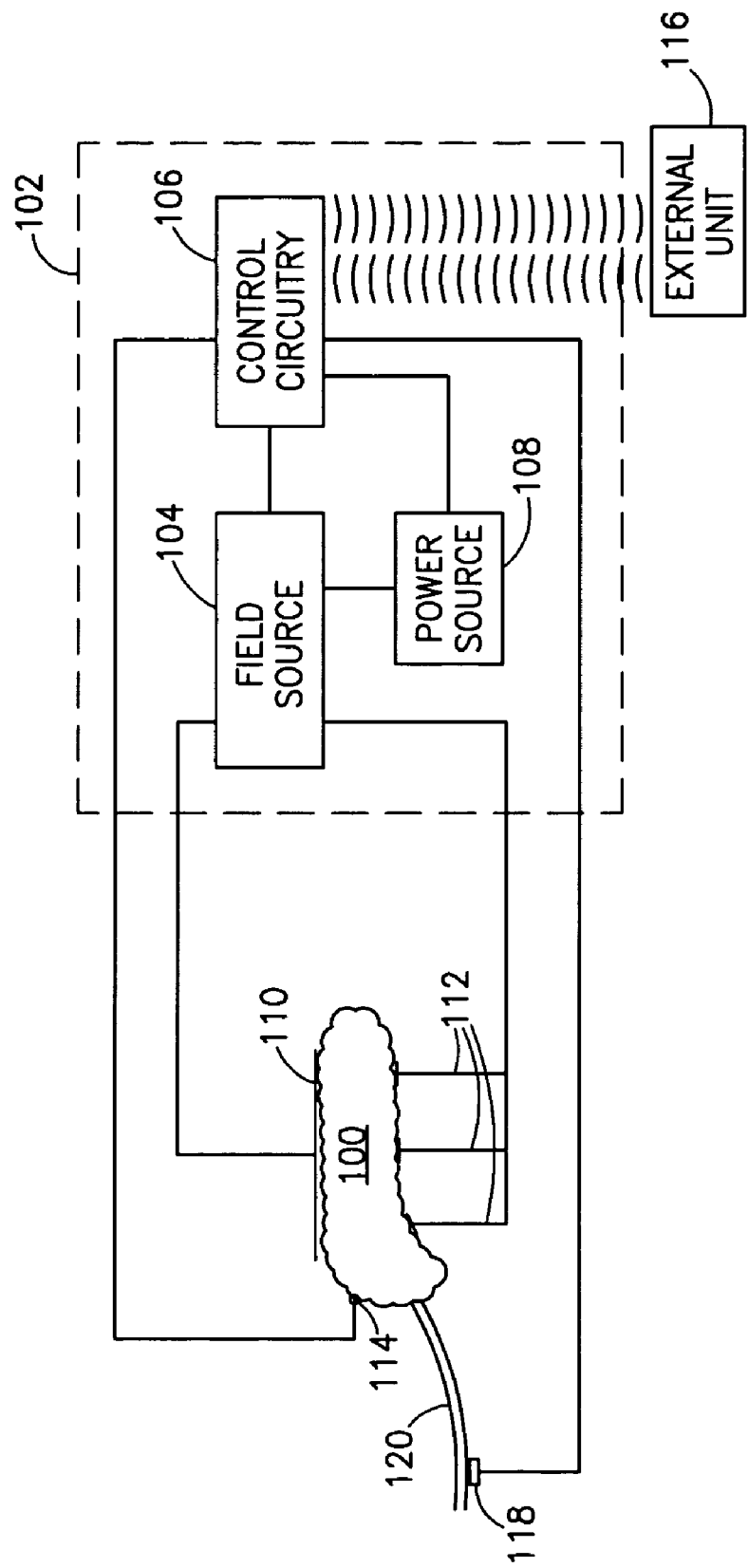
FIG. 1 is a block diagram of a pancreatic controller, in accordance with a preferred embodiment of the invention.

FIG. 1 is a block diagram of a pancreatic controller 102, in accordance with a preferred embodiment of the invention. In a preferred embodiment of the invention, device 102 is used to provide controlling pulses of electricity to a pancreas 100. Such controlling pulses may include excitatory stimulating pulses and non-excitatory pulses. In particular, such pulses can include pacing pulses and action potential modifying pulses.

In a preferred embodiment of the invention, the controlling pulses are used to control the glucose and insulin level of a patient. Further, a particular desired profile of glucose and/or insulin may be achieved. Other uses of controller 102 will be evident from the description below and can include, for example, training, healing and preventing damage of pancreatic cells.

Exemplary and non-limiting examples of metabolic and/or hormonal disorders that may be treated by suitable application of the methods described below, include non-insulin dependent diabetes mellitus, insulin dependent diabetes mellitus and hyperinsulemia.

The following description includes many different pulses that may be applied to achieve a desired effect, it should be clear that the scope of the description also covers apparatus, such as controller 102 that is programmed to apply the pulses and/or process feedback, as required. It should also be noted that a desired effect may be achieved by applying various combinations of the pulses described below, in to different sequences exemplars. The particular combinations of pulses that is appropriate for a particular patient may need to be determined on a patient by patient basis and may also change over time. Exemplary pulses and sequences, however, are described below.

Exemplary Device

Pancreatic controller 102, includes generally a field source 104 for generating electric fields across pancreas 100 or portions thereof, which field source is controlled by control circuitry 106. A power source 108 preferably powers field source 104 and control circuitry 106. The electrification is applied using a plurality of electrodes, for example a common electrode 110 and a plurality of individual electrodes 112. Alternatively other electrode schemes are used, for example a plurality of electrode pairs.

Electrical and other sensors may be provided as well, for input into controller 106. Although the electrodes may also serve as electrical sensors, in a preferred embodiment of the invention, separate sensors, such as a pancreatic sensor 114 or a glucose blood sensor 118 on a blood vessel 120, are provided. Extra-cellular sensors, for measuring inter-cellular glucose levels, may also be provided. Controller 102 may also include an external unit 116, for example for transmitting power or programming to control circuitry 106 and/or power source 108. Alternatively or additionally, the external unit may be used to provide indications from a patient and/or sensor information. Alternatively or additionally, the external unit may be used to provide alerts to the patient, for example if the glucose level is not properly under control. Alternatively or additionally, such alerts may be provided from inside the body, for example using low frequency sounds or by electrical stimulation of a nerve, a muscle or the intestines.

Additional details of this and other exemplary implementations will be provided below. However, the general structure of controller 102 may utilize elements and design principles used for other electro-physiological controllers, for example as described in PCT publications WO97/25098, WO 98/10831, WO98/10832 and U.S. patent application Ser. No. 09/260,769, the disclosures of which are incorporated herein by reference. It is noted, however, that the frequencies, power levels and duration of pulses in the pancreas may be different from those used, for example, in the heart. In particular, the power levels may be lower. Additionally, the immediate effects of an error in applying a pulse to the pancreas are not expected to be as life threatening as a similar error in the heart would be, excepting the possibility of tissue damage, which would cause an increase in severity of disease of the patient.

Tissue to Which the Controller is Applied

The present invention is described mainly with reference to pancreatic tissues. Such tissue may be in the pancreas or be part of an implant, possibly elsewhere in the body, or even in the controller envelope itself, the implant comprising, for example, homologous, autologus or hetrologus tissue. Alternatively or additionally, the implant may be genetically modified to produce insulin.

Electrical Activity in the Pancreas

Figure 2:
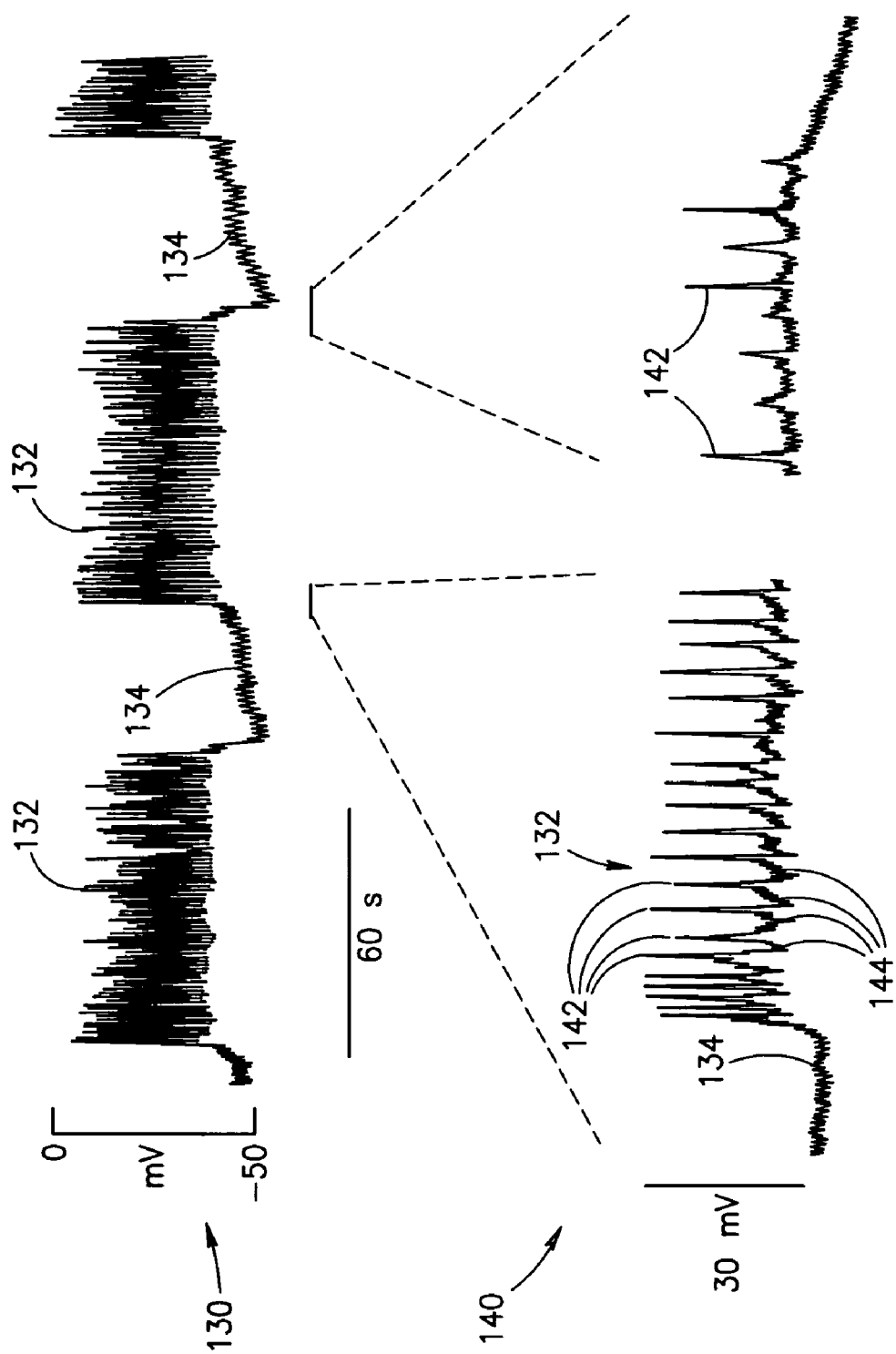
FIG. 2 is a diagram of an exemplary electrical activity of a single beta cell, operating at slightly elevated glucose levels.

FIG. 2 is a diagram of an exemplary electrical activity of a single beta cell, operating at slightly elevated glucose levels. In a large scale graph 130, the activity of a single cell is shown as comprising a plurality of burst periods 132 comprising a plurality of individual action potentials and separated by a plurality of interval periods 134, in which periods there are substantially no action potentials. As shown in a blow-up graph 140, each burst comprises a plurality of depolarization events 142, each followed by a repolarization period 144. The level of intra cellular calcium increases during the burst 132 and decreases during interval 134.

The beta cells of a pancreas are arranged in islets, each such islet acts as a single activation domain, in which, when the glucose levels are high enough, a propagating action potential is to be found. Thus, the aggregate electrical activity of an islet is that of a repeating average action potential, at a frequency, of for example, 1 Hz, which generally depends on the propagation time of an action potential through the islet. During intervals 134, if enough of the beta cells share the interval, the entire islet may be generally silent or contain only sporadic depolarization events.

Insulin Secretion Increase

The secretion of insulin, as differentiated from the production of insulin, may be increased in several ways, in accordance with preferred embodiments of the invention. The following methods may be applied together or separately. Also, these methods may be applied locally, to selected parts of the pancreas, or globally, to the pancreas as a whole.

In a first method, the duration of a burst 132 is increased, thus allowing more calcium to enter the beta cells. It is believed that the level of calcium in the cell is directly related to the amount of insulin released by the cell. One type of pulse which may be applied is a pacing pulse, which forces the cells in the islet to depolarize. Such a pulse is preferably applied at the same frequency as individual action potentials, e.g., 10 Hz. However, it may not be necessary to pace every action potential, a periodic pacing signal may be sufficient to force continuous depolarization events. As well known in the art of cardiac pacing, many techniques can be applied to increase the capture probability of the pacing signal, for example, double pacing, pulse shape and duration. These methods may also be applied, with suitable modifications, to the pacing of the pancreas. An alternative method of increasing burst length is by increasing the sensitivity of the beta cells to depolarization, for example, by sub-threshold pulses. Another method of sensitizing the cells and/or increasing their action potential duration is by hyperpolarizing the cells prior to a forced or normal depolarization. Possibly, by preventing the normal reduction in depolarization frequency towards the end of a burst, a higher insulin output can be achieved for a same length burst.

In another method of increasing insulin secretion is by increasing the calcium inflow efficiency of the individual action potentials. In a preferred embodiment of the invention, this is achieved by increasing the length of the plateau durations 144, for example by applying an electric pulse during the repolarization period associated with each of depolarization events 142. If such a pulse is applied early enough in the repolarization phase of an action potential, period, prior to closing of the calcium channels that provide the calcium inflow, these channels may stay open longer and will provide more calcium inflow. It is noted that the frequency of firing of the beta cells may be reduced.

In some cells, the calcium inflow may be more efficient during the depolarization period. In these cells, depolarization period 142 is preferably extended, for example by applying an additional depolarizing pulse during the depolarization or very shortly after. Alternatively or additionally, a pharmaceutical that enhances repolarization may be provided, so that the repolarization time is shorter and more of the duration of a burst 132 can be spent in depolarization events. Alternatively or additionally, a plateau duration can be shortened by applying a suitable pulse during the plateau. In one example, applying a pulse after the calcium channels close, is expected to shorten the repolarization time. Alternatively or additionally, the individual action potentials are paced, at a rate higher than normal for the glucose level. This pacing can override the end of repolarization and force more frequent depolarization events. It is noted that a considerably higher pacing rate can be achieved by pacing than would naturally occur for same physiological conditions. Possibly, the pacing rate is higher than physiologically normal for an islet at any glucose level.

In another method, the insulin secretion is enhanced by pacing the islets to have a higher frequency of bursts (as opposed to a higher frequency of action potentials, described above). The resulting shortening in intervals 134 may have undesirable effects, for example by maintaining high calcium levels in a cell for too long a period of time. In a preferred embodiment of the invention, this potential shortcoming is overcome by increasing the interval durations, for example, by applying a hyper-polarizing pulse during the interval, thus allowing calcium to leak out of the beta cells. It is noted however, that in some cases, sustained elevated calcium levels may be desirable. In which case, the intervals may be artificially shortened. In compensation, the effectiveness of the burst in causing the secretion of insulin may be reduced.

A potential advantage of pacing is that the pacing signal will cause depolarization and associated recruitment of beta cells that would not otherwise take part in the activity of the pancreas. It is expected that as intra-cellular calcium levels rise (or some other control mechanism), some cells will cease to participate in electrical activity. By applying a pacing pulse, such cells are expected to be forced to participate and, thus, continue to secret insulin.

Another potential advantage of pacing is related to the synchronization problem. As can be appreciated, some types of controlling pulses need to be applied at a certain phase in the cellular action potential. In a propagating action potential situation, it may be difficult to provide a single pulse with timing that matches all the cells, especially as the depolarization frequency increases. However, by forcing simultaneous depolarization of an entire islet, the phases are synchronized, making a desirable pulse timing easier to achieve. It is noted, however, that even if there is no pacing, some pulses, such as for extending a plateau of an action potentials, can be applied at a time that is effective for a large fraction of the cells in the islet.

Alternatively or additionally to calcium mediated vesicle transport, in a preferred embodiment of the invention, the electrical field also directly releases insulin from the REP of the cell and/or from other organelles in the cell.

Insulin Secretion Suppression

In some cases, for example if the glucose level is too low, suppression of insulin secretion may be desirable. Again, the following methods may be applied together or separately. Also, as noted above, different methods may be applied to different parts of the pancreas, for example, by differently electrifying electrodes 112 of FIG. 1, thus for example, increasing secretion from one part of the pancreas while decreasing secretion from a different part at the same time.

In a first method of insulin secretion reduction, the beta cells are hyper polarized, for example by applying a DC pulse. Thus, the cells will not respond to elevated glucose levels by depolarization and insulin secretion. It is noted that the applied pulse does not need to be synchronized to the electrical activity. It is expected that the hyper polarization will last a short while after the pulse is terminated. Possibly, only the length of the interval is increased, instead of completely stopping the burst activity.

In a second method, the insulin stores of the pancreas are dumped, so that at later times, the cells will not have significant amounts of insulin available for secretion. Such dumping may be performed for example, with simultaneous provision of glucose or an insulin antagonist, to prevent adverse effects. The insulin antagonist, glucose or other pharmaceuticals described herein may be provided in many ways. However, in a preferred embodiment of the invention, they are provided by external unit 116 or by an internal pump (not shown) in controller 102.

In a third method, the plateau durations 144 are shortened, for example by over-pacing the islet cells, so that there is less available time for calcium inflow. Alternatively, the intra-depolarization periods may be extended, by hyper-polarizing the cells during repolarization and after the calcium channels close (or forcing them closed by the hyper polarization). This hyper polarization will delay the onset of the next depolarization and thus, reduce the total inflow of calcium over a period of time.

Alternatively or additionally, a hyper-polarizing pulse may be applied during a burst, to shorten the burst.

Affecting Insulin Production

Various feedback mechanisms are believed to link the electrical activity of the beta cells and the production of insulin. In a preferred embodiment of the invention, these feedback mechanisms are manipulated to increase or decrease insulin production, alternatively or additionally to directly controlling insulin secretion.

In a preferred embodiment of the invention, beta cells are prevented from secreting insulin, for example, by applying a hyper-polarizing pulse. Thus, the intra-cellular stores remain full and less insulin is manufactured (and thus less insulin can reach the blood stream).

In a preferred embodiment of the invention, the beta cells are stimulated to release insulin. Depending on the cell, it is expected that if a cell is over stimulated, it is tired out and requires a significant amount of time to recover, during which time it does not produce insulin. If a cell is under stimulated, it is expected that it will, over time produce less insulin, as it adapts to its new conditions. If a cell is stimulated enough, it will continuously produce insulin at a maximal rate.

Pancreatic Response Control

In a preferred embodiment of the invention, rather than directly control insulin secretion levels, the response parameters of the pancreas are modified, to respond differently to glucose levels. One parameter that may be varied is the response time. Another parameter is the gain (amplitude) of the response. In some situations, these two parameters cannot be separated. However, it is noted that by providing complete control of the pancreas, many different response profiles can be provided by controller 102 directly.

In a preferred embodiment of the invention, the response time of the pancreas is increased or reduced by blocking or priming the fast-responding portions of the pancreas, in patients that have both fast and slow responding portions. Blocking may be achieved, for example, by partial or complete hyper-polarization. Priming may be achieved, for example, by applying a sub-threshold pulse, for example, just before depolarization. A potential advantage of such a sub-threshold pulse is that it may use less power than other pulses.

The gain of the response may be controlled, for example, by blocking or by priming parts of the pancreas, to control the total amount of pancreatic tissue taking part in the response. It is noted that priming "slow response" cells causes them to act as fast response cells, thereby increasing the gain of the fast response. In some cases, the priming and/or blocking may need to be repeated periodically, to maintain the sensitivity profile of the pancreas as described.

Alternatively or additionally, the sensitivity of the pancreas may be enhanced (or decreased) by supporting (or preventing) the propagation of action potentials, for example by providing a suitable pharmaceutical. Octonal and Heptonal are examples of pharmaceuticals that decouple gap junctions.

Exemplary Control Logic

Figure 3:
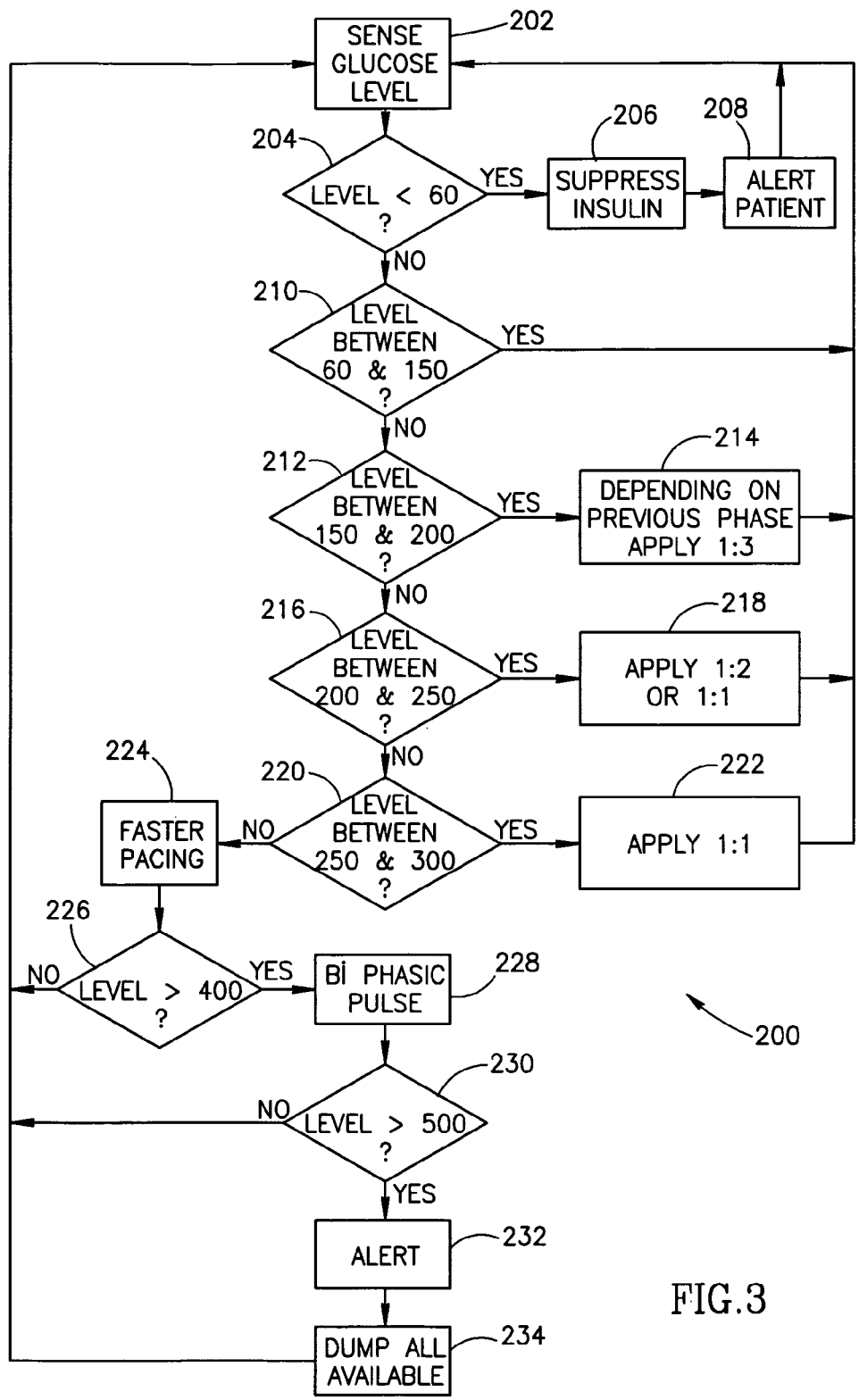
FIG. 3 is a flowchart of an exemplary control logic scheme, in accordance with a preferred embodiment of the invention.

FIG. 3 is a flowchart of an exemplary control logic scheme 200, in accordance with a preferred embodiment of the invention. In this scheme, the intensity of pancreatic activity (and associated dangers) is increased with the increase in glucose level. The various methods of increasing and decreasing pancreatic activity are described in more detail above or below. Alerts are preferably provided to the patient at extreme glucose levels. In addition, the method prefers to error on the side of causing hyperglycemia, whose adverse effects are less critical than those of hypoglycemia, whose adverse effects are immediate. It is noted than automated control logic for controlling glucose levels have been developed previously for insulin pumps and may also be applied for controller 102. An added ability of controller 102 is to suppress the body's own production of insulin. An added limitation which controller 102 preferably takes into account is the avoidance of damaging the pancreas by over stimulation.

In a step 202, the glucose level is determined. Many methods may be used to determine glucose level. In a preferred embodiment of the invention, in cases of hyperglycemia, the measurement is repeated several times before starting treatment. In cases of hypoglycemia, the measurements may be repeated few times or not at all, before starting treatment. The cycle of treatment is preferably repeated every two to five minutes. Alternatively, in critical situations such as hypoglycemia, the cycle is repeated even more frequently.

If the glucose level is under 60 (mg/dl) (step 204), further insulin production is preferably suppressed (206) and, optionally, the patient is alerted (208).

If the glucose level is between 60 and 150 (210), no action is taken, as these are normal glucose levels.

If the glucose level is between 150 and 200 (212), the action taken depends on the previous action taken and the previous measured glucose level. If, for example the previous level was higher, the insulin secretion activity may be maintained or reduced. If, on the other hand the glucose level was lower, the insulin secretion level may be increased. For example, a pulse application ratio of 1:3 between burst that are modified and bursts that are not modified may be provided if the glucose level is now reduced from its previous measurement. It should be appreciated, of course that the exact glucose levels and pulse parameters used for a particular patent will dependent only on the patient's medical history, but also on that patient's particular response to the pulse parameters used. Some patients may not responds as well as other patients and a more powerful pancreatic activity modification schedule used.

If the glucose level is between 200 and 250 (216), the action taken (218) can depend on the previous action taken for example providing a pulse application ratio between 1:1 and 1:2. Alternatively or additionally, the action taken can depend on the degree of change, direction of change and/or rate of change of glucose levels. Preferably, a model of insulin secretion, digestion and/or effect on blood glucose level are used to assess the significance of changes in glucose level.

If the glucose level is between 250 and 300 (220), an even higher pulse application rate, such as 1:1, can be applied (222).

Glucose levels higher than 300 can be quite dangerous. Thus, if such high rates are determined, a faster pacing rate, to the burst or to the individual action potentials (224), may be applied. Alternatively or additionally, a non-excitatory pulse to enhance secretion is also applied to at least some of the pacing pulses.

If the level is over 400 (226), a bi-phasic pacing pulse for the individual action potentials (228) may be provided. Such a pulse is expected at its first phase to induce depolarization and at its second phase to extend a plateau duration such that calcium inflow is increased. Alternatively or additionally, if not previous applied, control of multiple pancreatic regions may be provided, to increase the total portion of the pancreas being used to secret insulin at a higher rate.

If the glucose level is over 500 (230) emergency measures may be required, for example alerting the patient or his physician (232) and dumping all available insulin in the pancreas (234). A store of available insulin may be maintained in the pancreas or in device 102 (or an associated insulin pump) for just these cases.

It should be noted the above method is only exemplary. For example, the exact action at each may be modified, as can be the mixture of actions, the pulse parameters and the delays before changing action.

This control method utilizes delayed closed loop control circuits. Alternatively, open-loop circuits, which are similar to conventional glucose level management, may be provided. In such a loop, the amount of insulin output from a particular pulse application is known and is applied responsive to an infrequent measurement of the glucose level, for example using a blood test. Periodic glucose level testing may be applied to detect failed control. Intermediate control loops, control circuits having a smaller delay and combined control loops (having both open loop and closed loop) may be used in other preferred embodiments of the invention.

Long Term and Short Term Considerations

When applying electrification pulses in accordance with preferred embodiments of the invention, both short term and long term effects are preferably taken into considerations. Short term effects, include, for example effects on of insulin secretion and production. Long term effects include, for example, effects on tissue viability and capability and electrode polarization.

As will be described below, long terms effects may be negative, such as cell death, or positive, such as training or promoting healing.

Polarization and encrustation of the electrodes are preferably avoided by using ionic electrodes and applying balanced pulses (with substantially equal positive and negative charges). Alternatively, special coated electrodes, such as those coated with Iridium oxide or titanium nitride, may be used. Alternatively or additionally, relatively large electrodes may be used. The balancing may be on a per pulse basis or may be spread over several pulses.

In a preferred embodiment of the invention, controller 102 stores in a memory associated therewith (not shown) a recording of the glucose levels, the applied electrical and/or pharmaceutical control, food intake and/or the effect of the applied control on electrical activity of the pancreas and/or effects on the blood glucose level.

Cellular Training

In a preferred embodiment of the invention, the applied electrification and/or pharmaceutical profiles are used to modify the behavior of islet cells, in essence, training the cells to adapt to certain conditions. It is expected that slightly stressing a beta cell will cause the cell to compensate, for example by enlarging or by causing new beta cells to be produced. Such regeneration mechanism are known to exist, for example as described in "Amelioration of Diabetes Mellitus in partially Depancreatized Rats by poly(ADP-ribose) synthetase inhibitors. Evidence of Islet B-cell Regeneration", by Y Yonemura et. al, in *Diabetes*; 33(4):401-404, April 1984, the disclosure of which is incorporated herein by reference. Over stressing can kill the cell. Thus, the level of stress that enhances the cells' operation may need to be determined by trail and error for each patient. In a preferred embodiment of the invention, the trial and errors are performed on different parts of the pancreas, preferably with a bias to under-stressing rather than for over stressing. In a preferred embodiment of the invention, over stressing is determined by a marked reduction in insulin output or by reduced or abnormal electrical response.

Alternatively or additionally, a cell insensitive to medium glucose levels may be trained to be sensitive to lower glucose level, by exciting it more frequently and/or exciting it at times of slightly elevated glucose levels.

In a preferred embodiment of the invention, such training pulses are applied in combination with pharmaceuticals aimed to cause regeneration or healing.

It is noted that training and activation profile matching can also be used to maintain a cell in shape in a patient temporarily taking insulin, or to support a cell that is recuperating, for example from a toxic material or from the onset of diabetes.

Pulse Shapes and Parameters

The range of pulse forms that may be applied usefully is very wide. It must be noted that the response of the cells in different patients or of different cells in a same patient, even to same pulses, is expected to differ considerably, for example due to genetics and disease state. Also, the conduction of electrical signals in the vicinity of the pancreas is affected by the irregular geometrical form of the pancreas and the layers of fat surrounding it. These isolating layers may require the application of higher than expected amplitudes.

It is also noted that, at least for some embodiments, the application of the pulse is for affecting a certain portion of the pancreas and not the entire pancreas.

The lack of significant propagation of action potentials from one islet of the pancreas to another may require a relatively uniform field in the part of the pancreas to be affected. However, completely uniform fields are not required as any edge effects are contained only to the islets with the intermediate electric field strengths and/or because it is expected that the cell behavior does not vary sharply with the applied amplitude, except perhaps at certain threshold levels.

Further, the beta cells' behavior may be dependent on glucose level, on cellular insulin storage level and/or on previous activity of the cells. Unlike cardiac cells, which operate continuously and typically at a limit of their ability and/or oxygen usage, normal pancreatic cells are provided with long rests and are operated at sub-maximal levels.

A first parameter of the pulse is whether it is AC or DC. As the pulse may be applied periodically, the term DC pulse is used for a pulse that does not alternate in amplitude considerably during a single application, while an AC pulse does, for example having an intrinsic frequency an order of magnitude greater that 1/pulse duration. In a preferred embodiment of the invention, DC pulses or pulses having a small number of cycles per application, are used. In this usage, a pulse that is synchronized to a burst is considered AC if it alternates in amplitude, for example ten times over the burst duration, even though this frequency is actually lower than the action potential frequency. If, conversely, the pulse is a square pulse synchronized to the individual action potentials, it will be considered a DC pulse, for this discussion, although its actual frequency is higher than the AC pulse.

Exemplary frequencies for AC pulses applied to bursts are between 1 and 1000 Hz and for AC pulses applied to action potentials, between 20 and 2000 Hz. Preferably, the AC frequencies are between 50 and 150 Hz.

Various pulse durations may be used. An advantage of a DC long duration pulse is the lack of transients that might inadvertently affect other tissue. Such a pulse is expected to be useful for hyper-polarization of cells and, thus, may last for several seconds or even minutes or hours. Preferably however, very long duration pulses are interrupted and possibly, their polarity switched to prevent adverse effects such as tissue polarization near the electrodes or over-polarization of the target tissue.

A pulse for affecting a burst may last, for example, between 1 ms and 100 seconds. Exemplary durations are 10 ms, 100 ms and 0.5 seconds. Long pulses may be, for example 2 or 20 seconds long. A pulse for affecting a single action potential will generally be considerably shorter, for example being between 10 and 500 ms long. Exemplary durations are 20, 50 and 100 ms. However, longer pulses, such as 600 or 6000 ms long may also be applied.

In AC pulses, various duty cycles can be used, for example 10%, 50%, 90% and 100%. The percentages may reflect the on/off time of the pulse or they may reflect the relative charge densities during the on and off times. For example, a 50% duty cycle may be providing, on the average, 50% of the maximum charge flow of the pulse.

A pulse may be unipolar or bipolar. In a preferred embodiment of the invention, balanced pulses, having a total of zero charge transfer, are used. Alternatively, however, the balancing may also be achieved over a train of pulses or over a longer period. It is expected that at least for some pulse effects, the islets will act independently of the polarity of the applied pulse. However, changes in polarity may still have desirable effects, for example by creating ionic currents.

Different pulse envelopes are known to interact with cell membranes in different ways. The pulse envelope may be, for example, sinusoid, triangular, square, exponential decaying, bi-phasic or sigmoid. The pulse may be symmetric or asymmetric. Optionally, the pulse envelope is selected to take into account variations in tissue impedance during the pulse application and/or efficiency and/or simplicity of the power electronics.

In a preferred embodiment of the invention, the pulse current is controlled, for example to remain within a range. Alternatively or additionally, the pulse voltage is controlled, for example to remain within a range. Alternatively or additionally, both current and voltage are at least partly controlled, for example maintained in certain ranges. Possibly, a pulse is defined by its total charge.

Different types of pulses will generally, but not necessarily, have different amplitudes. The different effects of the pulse may also be a function of the cell activity phase and especially the sensitivity of the cell to electric fields at the time of application. Exemplary pulse amplitude types are sub-threshold pulses that affect the depolarization state of the cell and channel affecting pulses. These pulses are non-limiting examples of non-excitatory pulses, which do not cause a propagating action potential in the islet, either because of absolute low amplitude or due to relative low amplitude (relative to cell sensitivity). An islet current of 5 pA is suggested in the Medtronic PCT publication, for stimulating pulses.

Pacing pulses definitely cause a propagating action potential, unless the pacing pulse captures all the cells in the islet, in which case there may be nowhere for the action potential to propagate to.

"Defibrillation" pulses are stronger than pacing pulses and cause a rest in the electrical state of the affected cells.

Pore forming pulses, for example high voltage pulses, create pores in the membrane of the affected cells, allowing calcium to leak in or out and/or allowing insulin to leak out.

The above pulse types were listed in order of increasing typical amplitude. Exemplary amplitudes depend on many factors, as noted above. However, an exemplary pacing pulse is between 1 and 20 mA. An exemplary non-excitatory pulse is between 1 and 7 mA. A sub-threshold pulse may be, for example, between 0.1 and 0.5 mA. It is noted that the lack of excitation may be due to the timing of application of the pulse.

Simple pulse forms can be combined to form complex pulse shapes and especially to form pulse trains. One example of a pulse train is a double pacing pulse (two pulses separated by a 20 ms delay) to ensure capture of a pacing signal.

Another example of a pulse train is a pacing pulse followed, at a short delay, by a plateau extending pulse and/or other action potential control pulses. Thus, not only is pacing forced, possibly at a higher than normal rate, but also the effectiveness of each action potential is increased. The delay between the pacing pulse and the action potential control pulse can depend, for example, in the shape of the action potential and especially on the timing of opening and closing of the different ionic channels and pumps. Exemplary delays are 10, 50, 200 and 400 ms.

Pulse Timings

Not only are various pulse forms contemplated, also different variations in their periodicy are contemplated.

A first consideration is whether to synchronize an excitatory and/or a non-excitatory pulse to the pancreatic activity or not. If the pulse is synchronized, it can be synchronized to the activity of particular cells or islets being measured. As noted above, a pacing pulse to the pancreas can force synchronization. The pulse may be synchronized to individual action potentials and/or to burst activity. Within an action potential, the pulse can be synchronized to different features of the action potential, for example the depolarization, plateau, repolarization and quiescent period before depolarization. Not all action potentials will exhibit exactly these features.

Within a burst, a pulse may be synchronized to the start or end of the burst or to changes in the burst envelope, for example, significant reductions in the action potential frequency or amplitude.

As used herein, synchronization to an event includes being applied at a delay relative to the event occurring or at a delay to when the event is expected to occur (positive or negative delay). Such a delay can be constant or can vary, for example being dependent on the action potential or the burst activity.

The pulse may be applied at every event to which it is synchronized for example every action potential or every burst. Alternatively, pulses are applied to fewer than all events, for example at a ratio of 1:2, 1:3, 1:10 or 1:20. An exemplary reason for reducing the pulse application ratio is to prevent overstressing the beta cells and causing cellular degeneration, or to provide finer control over secretion rate.

In some pulses, a significant parameter is the frequency of application of the pulse (as differentiated from the frequency of amplitude variations in a single pulse). Exemplary frequencies range from 0.1 HZ to 100 Hz, depending on the type of pulse.

In a preferred embodiment of the invention, the pulse parameters depend on the islet or cellular electrical and/or physiological state. Such a state may be determined, for example using suitable sensors or may be estimated from a global state of the glucose level.

Sensors

Many types of sensors may be usefully applied towards providing feedback for controller 102, including, for example:

(a) Glucose sensors, for example for determining the actual glucose level and providing feedback on the effects of the pancreatic treatment. Thus, for example, in a patient with weakened pancreatic response, the pancreas will be stimulated to secrete more insulin when the glucose levels are too high. Many types of glucose sensors are known in the art and may be used for the purposes of the present invention, including, for example optical, chemical, ultrasonic, heart rate, biologic (e.g., encapsulated beta cells) and electric (tracking beta cell and/or islet electrical behavior). These sensors may be inside the body or outside of it, connected to controller 102 by wired or wireless means, be in contact with the blood or outside of blood vessels.

(b) Digestion sensors, for example for detecting the ingestion—or upcoming intake—of meals, and, for example, prompting the production of insulin or increase in cell sensitivity. Many suitable sensors are known in the art, for example impedance sensors that measure the stomach impedance, acceleration sensors that measure stomach or intestines movements and electrical sensors that measure electrical activity. Digestion sensing cells are inherently problematic if they do not provide a measure of glucose actually ingested. Preferably, they are used in combination with other sensors and/or only if the digestion system is activated in a profile matching eating, for example a long duration activation or activation that advances along the digestive system. In a preferred embodiment of the invention, stimulation during the digestion may be stopped, to at least some parts of the pancreas (e.g., ones comprising fewer islets), to avoid interfering with other cell types in the pancreas, for example those that produce digestive juices. Alternatively or additionally, the application of stimulation in general may be optimized to reduce interaction with non-beta cells, for example alpha cells. As alpha cells generate glucagon, their stimulation may be determined by tracking serum glucagon levels.

(c) Pancreatic activity sensors, for example electrodes coupled to the entire pancreas, small parts of it, individual islet(s) or individual cell(s) in an islet. Such sensors are useful not only for providing feedback on the activity of the pancreas and whether the applied pulses had a desired electrical (as opposed to glucose-) effect, but also for synchronizing to the pancreatic electrical activity.

(d) Calcium sensors, both for intracellular spaces and for extra-cellular spaces. As can be appreciated, measuring calcium inside a cell may affect the behavior of the cell. In a preferred embodiment of the invention, only one or a few cells are used as a sample for the state of the other cells. An exemplary method of intracellular calcium measurement is to stain the cell with a calcium sensitive dye and track its optical characteristics. It is noted that both intra- and extra-cellular calcium levels may affect the electrical and secretary activity of beta cells.

(e) Insulin sensors, of any type known in the art may be used to measure the response of a single islet, the pancreas as a whole and/or to determine blood levels of insulin.

The measurements of the above sensors are preferably used to modify the pulse parameters or pulse application regime. Alternatively or additionally, the sensors are used to track the response to the regime and/or lack of application of pulses, or for calibration.

Different sensing regiments may be use, including continuous sensing, and periodic sensing. Some sensors may provide a frequent measurement, for example every few seconds or minutes. Other sensors may be considerably slower, for example taking a measurement every ten minutes or hour. If only a periodic measurement is required, the measurement may be an average over the time between measurements or it may be an average over a shorter time or an instantaneous value. In some cases a long term integrative sensing, for example of total insulin production, is desirable. A one-time chemical sensor may be suitable for such integrative sensing.

Types of Electrodes

The electrodes used may be single functionality electrodes, for example only for pacing or only for non-excitatory pulses. Also, different types of non-excitatory pulses, such as hyperpolarization and plateau extension pulses, may use different types of electrode geometries. Alternatively, a combination electrode, comprising both a pacing portion and a pulse application portion, may be provided. The different types of electrodes may have different shapes, for example due to the pacing electrode being designed for efficiency and the pulse electrode being designed for field uniformity. The two electrode functions may share a same lead or them may use different leads. Alternatively, a single electrode form is used for both pacing and non-excitatory pulse application.

FIGS. 4A-4D illustrate different types of electrodes that may be suitable for pancreatic electrification, in accordance with preferred embodiments of the invention.

Figure 4A:
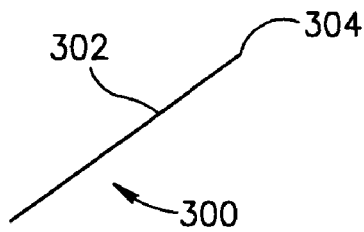
FIGS. 4A-4D illustrate different types of electrodes that may be suitable for pancreatic electrification, in accordance with preferred embodiments of the invention.

FIG. 4A illustrates a point electrode 300 having a single electrical contact area at a tip 304 of a lead 302 thereof.

Figure 4B:
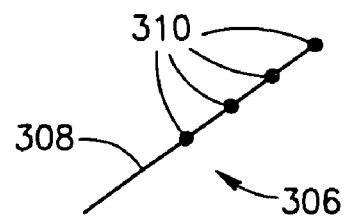

FIG. 4B illustrates a line electrode 306 having a plurality of electric contacts 310 along a length of a lead 308 thereof. An advantage of wire and point electrode is an expected ease in implantation using endoscopic and/or other minimally invasive techniques. In a preferred embodiment of the invention, multiple wire electrodes are implanted.

Figure 4C:
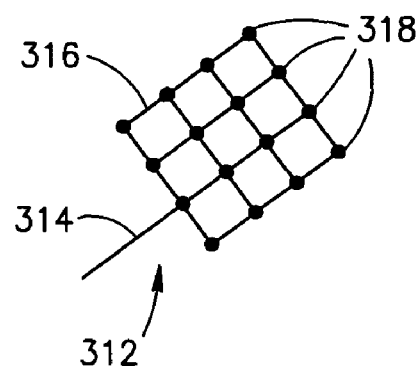

FIG. 4C illustrates a mesh electrode 312, including a lead 314 and having a plurality of contact points 318 at meeting points of mesh wires 316. Alternatively or additionally, some of the wire segments between meeting points provide elongate electrical contacts.

Each of the contact points can be made small, for example slightly larger than an islet. Alternatively, larger contact areas are used. In line electrodes, exemplary contact areas are 0.2, 0.5, 1, 2 or 5 mm long. In some embodiments of the invention, smaller contact areas than used for cardiac pacemakers may be suitable, as smaller fields may be sufficient.

Figure 4D:
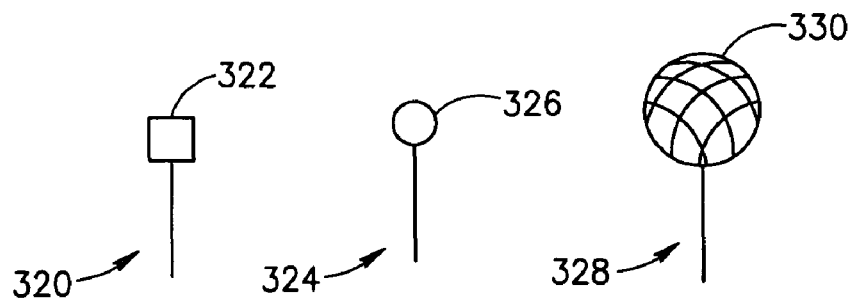

In some embodiments, volume excitation of the pancreas is desired. FIG. 4D illustrates various volume excitation electrodes. A plate electrode 320 includes a plate 322 that can simultaneously excite a large area. A ball electrode 324 includes a ball shaped contact area 326, with a radius of, for example, 2 or 4 mm, for exciting tissue surrounding ball 326. A hollow volume electrode 328, for example, includes an open volume contact area 330, for example a mesh ball or a goblet, which cane be used to excite tissue in contact with any part of ball 330, including its interior. Another possibility is a coil electrode. Preferably, the coils have a significant radius, such as 2 or 5 mm, so they enclose significant pancreatic tissue. It is noted that volume (and other electrodes as well) electrodes may encompass a small or large part of the pancreas or even be situated to electrify substantially all the insulin producing parts of the pancreas.

Any of the above electrodes can be unipolar or bipolar. In bipolar embodiments, a single contact area may be spilt or the bi-polar activity may be exhibited between adjacent contact points.

In addition, the above multi-contact point electrodes may have all the contact points shorted together. Alternatively, at least some of the contact points can be electrified separately and, preferably, independently, of other contact points in a same electrode.

Electrical contact between an electrode an the pancreas can be enhanced in many ways, for example using porous electrode, steroids (especially by using steroid eluting electrodes) and/or other techniques known in the art. The type of electrode may be any of those known in the art and especially those designed for long term electrical stimulation.

Figure 4E:
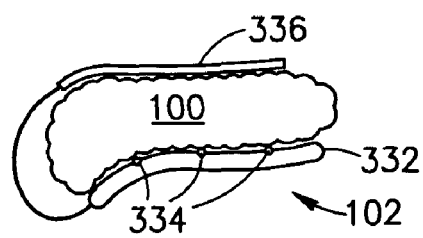
FIG. 4E illustrates an electrode, in which the body of the controller of FIG. 1 serves as at least one electrode, in accordance with a preferred embodiment of the invention.

FIG. 4E illustrates a different type of electrode, in which a casing 332 of controller 102 serves as one or multiple electrodes. Casing 332 may be concave, convex or have a more complex geometry. Possibly, no external electrodes outside of casing 332 are used. Preferably, casing 332 is then made concave, to receive the pancreas. Alternatively, at least a common electrode 336 outside of controller 102 is provided. Alternatively or additionally, casing 332 of controller 102 serves as a common electrode. In a preferred embodiment of the invention, a plurality of electrodes 334 are formed in casing 332. The electrode types can be any of those described above, for example. Preferably, but not necessarily, electrodes 334 stick out of casing 332. In a preferred embodiment of the invention, controller 102 is placed in contact with pancreas 100, as an electrically insulating layer of fat usually encapsulates the pancreas. Preferably, the geometry of casing 332 is made to conform to the shape of the pancreas, thus assuring contact with the pancreas and minimal trauma to the pancreas by the implantation. Optionally, a flexible or multi-part hinged casing is provided, to better conform the casing to the pancreas.

The electrodes can be fixed to the pancreas in many means, including, for example, using one or more sutures or clips, providing coils or roughness in the electrode body, using adhesive or by impaling the pancreas or nearby tissue. An electrode may include a loop, a hole or other structure in it for fixing the suture or clip thereto. It is noted that the pancreas does not move around as much as the heart, so less resilient electrode and lead materials and attachment methods may be used.

Various combinations of the above electrodes may be used in a single device, for example a combination of a mesh electrode underneath the pancreas and a ground needle electrode above the pancreas. Such a ground electrode may also be inserted in nearby structures, such as the abdominal muscles.

As described below, the pancreas may be controlled as plurality of controlled regions. A single electrode may be shared between several regions. Alternatively or additionally, a plurality of different electrodes may be provided for the different regions or even for a single region.

Pancreatic Control Regions

Figure 5:
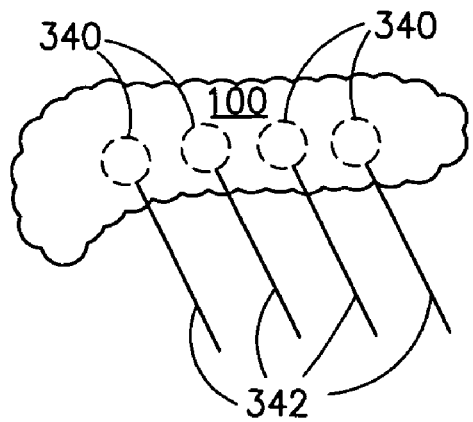
FIG. 5 illustrates a pancreas subdivided into a plurality of control regions, each region being electrified by a different electrode, in accordance with a preferred embodiment of the invention.

FIG. 5 illustrates a pancreas subdivided into a plurality of control regions 340, each region being electrified by a different electrode 342. Control regions 340 may overlap (as shown) or they may be none-overlapping. Possibly, the entire pancreas is also a control region, for example for insulin secretion suppression. Although a significant percentage of the pancreas is preferably controlled, for example 10%, 20%, 40% or 60%, part of the pancreas may remain uncontrolled, for example as a control region or as a safety measure. The number of control regions can vary, being for example, two, three, four, six or even ten or more.

One possible of different control regions is to allow one part of the pancreas to rest while another part is being stimulated to exert itself. Another possible use is for testing different treatment protocols on different regions. Another possible use is to provide different control logic for parts of the pancreas with different capabilities, to better utilize those regions or to prevent damage to those reasons. For example, different pulses may be applied to fast responding or slow responding portions. In addition, some parts of the pancreas may be more diseased than other parts.

Optionally, the density and/or size of the electrodes placement on the pancreas (And independently controllable parts of the electrodes) varies and is dependent, for example, on the distribution and density of islet cells in the pancreas. For example, a more densely populated section of the pancreas may be provided with finer electrical control. It is noted that the distribution may be the original distribution or may be the distribution after the pancreas is diseased and some of the cells died or were damaged.

Implantation Method

The implantation of controller 102 can include implantation of electrodes and implantation of the controller itself. Preferably, the two implantations are performed as a single procedure. However, it is noted that each implantation has its own characteristics. Implanting a small casing into the stomach is a well-known technique and may be performed, for example using a laproscope, using open surgery or using keyhole surgery.

Implantation of electrodes in the pancreas is not a standard procedure. Preferably, elongate, uncoiling or unfolding electrodes are used so that electrode implantation is simplified.

In a preferred embodiment of the invention, the electrodes are implanted using a laproscopic or endoscopic procedure. Preferably, also controller 102 is inserted using a laproscope or endoscope. In a preferred embodiment of the invention, the geometry of controller 102 is that of a cylinder, so it better passes through an endoscope (flexible, relatively narrow diameter tube) or a laproscope (rigid, relatively large diameter tube). Alternatively, controller 102 is implanted separately from the electrodes. In one example, the electrodes are implanted with a connection part (e.g., wire ends) of the electrodes easily available. A second entry wound is made and the controller is attached to the connection parts. Possibly, the electrodes are implanted connection part first. Alternatively, after the electrodes are implanted, the endoscope is retracted, leaving the connection part in the body.

Figure 6A:
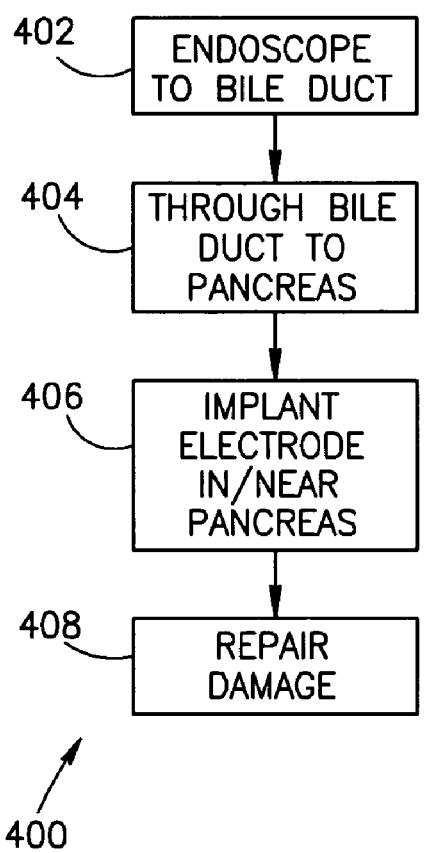
FIGS. 6A and 6B are flowcharts of implantation methods, in accordance with preferred embodiments of the invention.
Figure 6B:
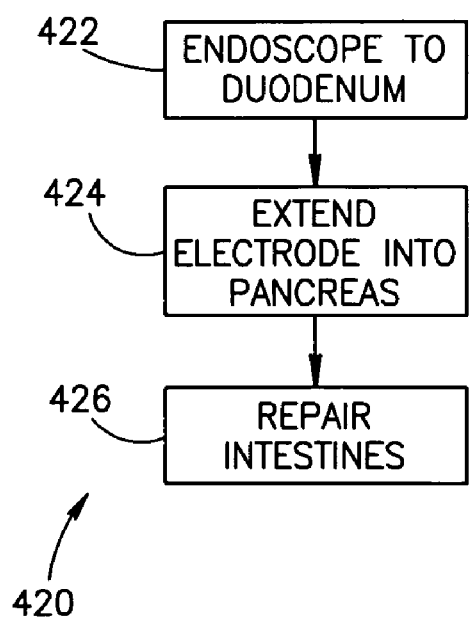

FIGS. 6A and 6B are flowcharts of implantation methods, in accordance with preferred embodiments of the invention.

FIG. 6A is a flowchart 400 of a bile duct approach. First, an endoscope is brought to a bile duct, for example through the stomach (402). The endoscope then enters the bile duct (404) for example using methods known in the art. As shown, the endoscope may travel though the bile ducts along the pancreas. Alternatively, the electrodes may be provided by a catheterization of the splenic artery or vein. Alternatively, the portal vein may be catheterized, for example via a laproscopic opening in the abdomen. The electrodes are implanted in, or alongside, the pancreas, for example in the blood vessels or the bile ducts, the pancreas being an elongated gland (406). In a preferred embodiment of the invention, the endoscope (or an extension thereof) is first advanced to the far end of the pancreas, the electrodes are attached to the pancreas and then the endoscope is retracted, leaving the electrodes behind. Alternatively, the electrodes may be advanced out of the pancreas, by themselves or using a relative rigid and/or navigable jacket. Preferably, but not necessarily, imaging techniques, such as light, ultrasound or x-ray imaging, are used to track the electrode and/or the endoscope. The imaging may be from outside the body or from inside the body, for example from the tip of the endoscope.

Any damage to body structures is preferably repaired during endoscope/catheter retraction (408). Alternatively, other arterial and/or venous techniques may be used. In some techniques, controller 102 is implanted and then the electrodes are guided along or inside a blood vessel or other body structure to the pancreas.

In bile duct implantation, a special coating may be provided on the electrode or leads, to protect against the bile fluids. The contact part of the electrode may be embedded in tissue to prevent bile fluid damage thereto.

FIG. 6B is a flowchart 420 of an alternative implantation method. An endoscope is advanced to the duodenum or other part of the intestines adjacent the pancreas (422). Electrodes are extended from the intestines into the pancreas (424), while controller 102 remains in the intestines. The electrodes may also extend part way along the inside of the intestines. Electrodes on the far side of the pancreas may be implanted from a different part of the intestines or they pass through the pancreas. Alternatively, also the controller is pushed out through a hole formed in the side of the intestines. Alternatively, the controller is enclosed in a pocket of the intestines, the pocket preferably formed by suturing or clipping together part of the intestines. Alternatively, the controller is attached to the intestines, for example using clips or using sutures. Any damage to the intestines may then be repaired (426).

As noted above with reference to FIG. 1, controller 102 may be a wireless device, with the control circuitry separate from the electrodes. The electrodes can have individual power sources or they may be powered (or recharged) using beamed power.

In an alternative embodiment, controller 102 is a multi part device, for example comprising a plurality of mini-controllers, each mini controller controlling a different part of the pancreas. The activities of the mini-controllers may be synchronized by communication between the controllers or by a master controller, for example in the separate, possibly external unit 116. Unit 116 may directly synchronize the mini controllers and/or may provide programming to cause them to act in a synchronized manner. An exemplary geometry for a mini-controller is that of two balls connected by a wire. Each ball is an electrode, one ball contains a power source and the other ball contains control circuitry. Communication between the mini controllers may be, for example using radio waves, preferably low frequency, or using ultrasound. Suitable transmitter and/or receiver elements (not shown) are preferably provided in the mini-controllers.

Alternatively to an implanted controller, the controller may be external to the body with the electrodes being inserted percutaneously to the pancreas, or even remaining on the out side of the body. Alternatively, the controller and the electrodes may be completely enclosed by the intestines. These "implantation" methods are preferred for temporary use of the device.

In some cases, proper implantation of sensors may be problematic, for example sensors that impale single beta cells or islets. In an optional procedure, part of the pancreas is removed, sensors and/or electrodes are attached thereto and then the removed part is inserted back into the body.

In the above embodiments, it was suggested to impale the pancreas using electrodes or electrode guides. In a preferred embodiment of the invention, when impaling, care is taken to avoid major nerves and blood vessels. In a preferred embodiment of the invention, the implantation of electrodes takes into account other nearby excitable tissue and avoids inadvertent stimulation of such tissue.

Calibration and Programming

Pancreatic controller 102 may be implanted not only, after a stable disease state is known, but also during an ongoing disease progression. Under these conditions and even in the steady state, cells that are to be controlled by controller 102 are expected to be diseased and/or over-stressed and may behave somewhat unpredictably. Thus, in a preferred embodiment of the invention, optimizing the control of the pancreas may require calibrating the controller after it is implanted. However, it is noted that such calibration is not an essential feature of the invention and may even be superfluous, especially if a reasonable estimate of the pancreatic physiological state can be determined before implantation.

Figure 7:
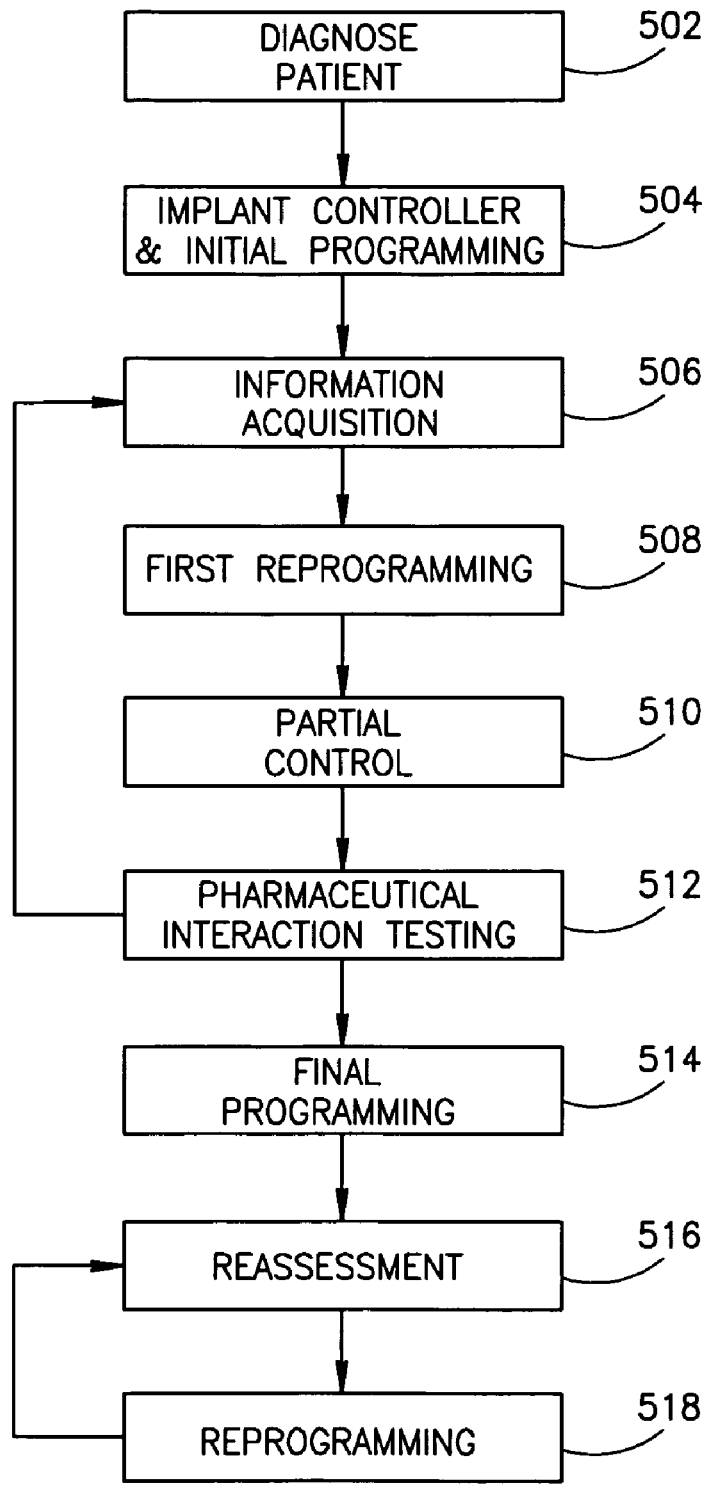
FIG. 7 is a flowchart of an exemplary method of controller implantation and programming, in accordance with a preferred embodiment of the invention.

FIG. 7 is a flowchart 500 of an exemplary method of controller implantation and programming, in accordance with a preferred embodiment of the invention. Other methods may also be practiced.

Before implantation, a patient is preferably diagnosed (502) and an expected benefit of implantation is preferably determined. It is noted however, that controller 102 may also be used or diagnostic purposes, due to its ability to take measurements over extended periods of time and determining the response of the pancreas cells to different stimuli and situations.

A controller is then implanted, for example as described above, and an initial programming provided (504). The initial programming may be performed while the controller is outside the body. However, In a preferred embodiment of the invention, the controller is capable of extensive programming when inside the body, for example as described below, to enable the controller to selectively apply one or more of the many different logic schemes and pulses, possibly differently to one or more of the controlled areas.

During an information acquisition step (506) the behavior of the pancreas is tracked, possibly without any active control of the pancreas. This information acquisition preferably continues all through the life of the controller. In a preferred embodiment of the invention, the acquired information is periodically- and/or continuously-reported to a treating physician, for example using external unit 116. An exemplary report is the glucose levels in the body and the main events that affected the glucose level.

Alternatively to mere information gathering, the information acquisition also uses test control sequences to determine the pancreatic response to various pulse forms and sequences.

In a preferred embodiment of the invention, the information acquisition step is used to determine physiological pathologies and especially to detect and feedback- and/or feed-forward-mechanisms that are impaired. Such mechanisms are preferably supplemented, replaced and/or overridden by controller 102.

In a preferred embodiment of the invention, various protocols are tried on small control regions to determine their effect.

The information acquisition, and later the calibration and programming may be performed on a per-person basis or even on a per-islet or per pancreatic portion basis. Preferably, a base line programming is determined from other patients with similar disorders.

Optionally, various test sequences are timed to match patient activities such as eating, sleeping, exercising and insulin uptake. Also the programming of the controller may be adapted to a sleep schedule, meal taking schedule or other known daily, weekly or otherwise periodic activities.

After a better picture of how the pancreas is acting is formed, a first reprogramming (508) may be performed. Such reprogramming may use any means known in the art such as magnetic fields and electromagnetic waves.

The reprogramming preferably implements partial control of the pancreas (510). Such partial control may be used to avoid overstressing the entire pancreas. Some of the controlled parts may be suppressed, for example using hyperpolarizing pulses as described above. It is noted however, that since the pancreatic damage does not usually cause immediate life threatening situations and because the pancreas is formed of a plurality of substantially independent portions, there is considerably more leeway in testing the effect of control sequences and even the long term effects of such sequences, that there is in other organs such as the heart.

In an optional step 512, the interaction of pharmaceutical or hormonal treatment with the controller may be determined. In this context is it noted that cardiac and nerve electrophysiological pharmaceuticals may be useful also for treatment of pancreatic disorders. Alternatively, pancreatic control may be desirable to offset negative side effects of such pharmaceuticals taken for non-metabolic disorders.

Steps 508-512 may be repeated a plurality of times before settling down to a final programming 514. It is noted that even such final programming may be periodically re-assessed (516) and then modified (518), for example, as the pancreas and/or the rest of the patient improves or degrades, or to apply various long-term effect control sequences.

In a preferred embodiment of the invention, a tissue viability testing of the controlled and or/uncontrolled parts of the pancreas is preferably performed periodically, for example to assess patient state, to update the patient base line and to assess the efficiency of the therapy. Exemplary methods of viability testing include analyzing electrical activity, responses to changes in glucose level or insulin levels and/or responses to various types of electrical stimulation.

In a preferred embodiment of the invention, the programming, measurements and/or prior attempted treatments (including possibly pharmaceutical treatments) are stored in a memory portion of controller 102. Alternatively or additionally, the programming may include special sequences that take into account taking of pharmaceuticals. In a preferred embodiment of the invention, when a patient takes a pharmaceutical or insulin controller 102 is notified, for example by manual input into external unit 116 or automatically by the administration method. If the patient neglected to take the pharmaceutical, insulin, and/or glucose, a compensatory control sequence is provided, possibly irrespective of whether an alert is provided to the patient.

Experiment

In an exemplary experiment, a mesh unipolar electrode was placed under a pig pancreas and a needle electrode was inserted into the overlying abdominal wall as a ground. A pulsed current (5 Hz, 5 mA, 5 ms duration) was applied for five minutes and resulted in decrease in serum glucose from 89 to 74 mg/dl. Serum insulin increased from 3.8 to 5.37, microU/ml, measured using the ELISA method. Both glucose levels and insulin levels returned to the baseline after 30 minutes. in a different animal, the application for 5 minutes of a pulse of 3 Hz, 12 mA and 5 ms duration resulted in an insulin increase from 8.74 microU/ml to 10.85 8.74 microU/ml.

Figure 8:
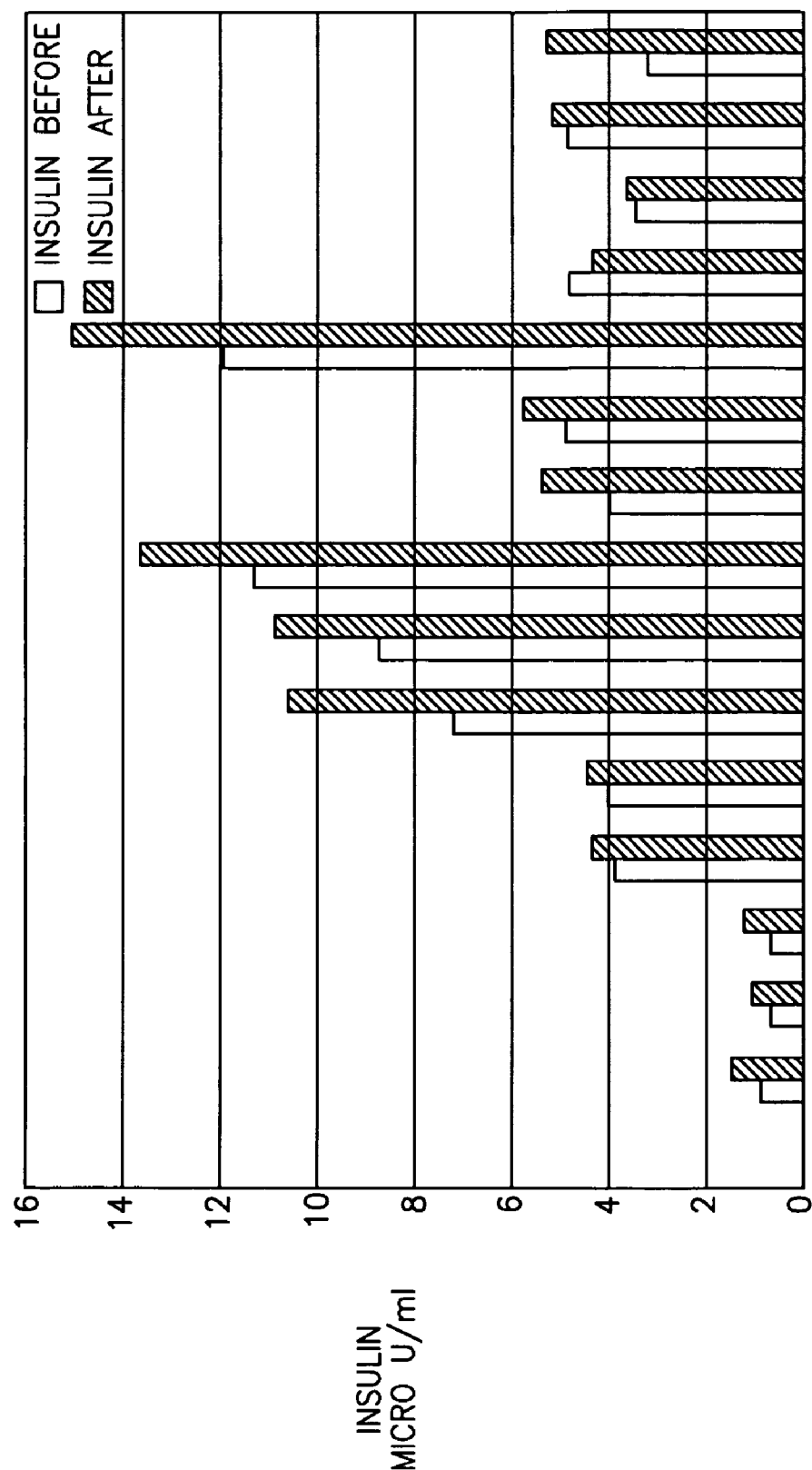
FIG. 8 is a chart showing the effect of electrical stimulation on insulin levels, in six animals.

FIG. 8 is a chart showing the effect of such electrical stimulation on insulin levels, in six animals.

Exemplary Applications

The above pancreatic controller 102 may be used after a diabetic state is identified. Preferably however, the controller is used to better diagnose an evolving disease state and/or to prevent a final diabetic state from ever occurring, for example by supporting the pancreas. Thus, a temporary device embodiment is preferably provided additionally to permanently implanted device.

In another application, strict control of body insulin output and blood glucose levels is used not only to prevent obese patient from developing diabetes by overworking of the pancreas, but also (simultaneously or alternatively) for reducing body weight. Such a scheme may require strict prevention of elevated glucose levels in blood, to avoid damage to the body. However, it is expected that by reducing insulin production at "normal" glucose levels, feelings of hunger may be suppressed, as well as reducing the increase in mass of adipose tissue.

In a preferred embodiment of the invention, controller 102 is a stand alone device. However, a dual organ controller may be useful in some disease states. In one example, it is noted that many patients with pancreatic disorders also have cardiac problems. Thus, a combined cardiac/pancreatic controller may be provided, possibly sharing one or more of a casing, programming means, power supply and control circuitry. In another example, a controller for the uterus and a pancreatic controller may be combined to protect against pregnancy related diabetes and improper uterine contractions.

Another exemplary dual organ controller is used for both the stomach and the pancreas. Such a controller is useful for obese persons, to suppress stomach contractions and prevent feelings of hunger. At the same time, insulin level may be controlled to prevent hunger, or, in diabetic patients, to prevent hyper- or hypo-glycemia.

It will be appreciated that the above described methods of controlling a pancreas may be varied in many ways, including, changing the order of steps, which steps are performed more often and which less often, the arrangement of electrodes, the type and order of pulses applied and/or the particular sequences and logic schemes used. Further, the location of various elements may be switched, without exceeding the sprit of the disclosure, for example, the location of the power source. In addition, a multiplicity of various features, both of method and of devices have been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. In addition, some of the features of the invention described herein may be adapted for use with prior art devices, in accordance with other preferred embodiments of the invention. The particular geometric forms used to illustrate the invention should not be considered limiting the invention in its broadest aspect to only those forms, for example, where a ball electrode is shown, in other embodiments an ellipsoid electrode. Although some limitations are described only as method or apparatus limitations, the scope of the invention also includes apparatus programmed and/or designed to carry out the methods, for example using firmware or software programming and methods for electrifying the apparatus to have the apparatus's desired function.

Also within the scope of the invention are surgical kits which include sets of medical devices suitable for implanting a controller and such a controller. Section headers are provided only to assist in navigating the application and should not be construed as necessarily limiting the contents described in a certain section, to that section. Measurements are provided to serve only as exemplary measurements for particular cases, the exact measurements applied will vary depending on the application. When used in the following claims, the terms "comprises", "comprising", "includes", "including" or the like means "including but not limited to".

It will be appreciated by a person skilled in the art that the present invention is not limited by what has thus far been described. Rather, the scope of the present invention is limited only by the following claims.

The invention claimed is:

1. A method of controlling body glucose levels, comprising:
    implanting an electrode adapted to electrify at least a part of an abdominal region of a person having a pancreas with existing electrical activity; and
    applying an AC pulse via said electrode to the abdominal region, without synchronizing said applying to said existing electrical activity, which pulse causes a reduction in glucose levels in a body containing said pancreas,
    wherein said implanting comprises attaching to a muscle and wherein applying comprises avoiding inadvertent excitation of said muscle.

2. A method of controlling insulin secretion, comprising:
    implanting an electrode adapted to electrify at least a part of an abdominal region of a person having a pancreas with existing electrical activity; and
    applying an AC pulse via said electrode to the abdominal region, without synchronizing said applying to said existing electrical activity, which pulse modifies an insulin response of said pancreas to glucose levels,
    wherein said implanting comprises attaching to a muscle and wherein applying comprises avoiding inadvertent excitation of said muscle.

3. A method according to claim 1, wherein said AC pulse includes a symmetric pulse.

4. A method according to claim 1, wherein said AC pulse includes an asymmetric pulse.

5. A method according to claim 1, wherein said AC pulse includes a bi-phasic pulse.

6. A method according to claim 1, wherein said AC pulse includes a pulse train.

7. A method according to claim 6, wherein said pulse train includes delays.

8. A method according to claim 1, wherein said AC pulse is excitatory at least in part.

9. A method according to claim 1, wherein said AC pulse is non-excitatory.

10. A method according to claim 1, wherein said AC pulse includes at least one excitatory pulse followed by at least one non-excitatory pulse.

11. A method according to claim 1, comprising determining an ingestion event, wherein said applying is in response to said determined ingestion.

12. A method according to claim 1, comprising anticipating an ingestion event wherein said applying is in response to said anticipated ingestion.

13. A method according to claim 1, said electrode is adapted for being placed adjacent said pancreas.

14. A method according to claim 1, wherein said electrode is adapted for long term contact with bile fluids.

15. A method according to claim 1, wherein said AC pulse is designed to extend a plateau duration of an action potential of a cell in the abdominal region, thereby allowing more calcium inflow into the cell.

16. A method according to claim 1, wherein said AC pulse is designed to extend a duration of a burst activity of cells in said abdominal region.

17. A method according to claim 1, wherein said AC pulse has an amplitude sufficient to recruit non-participating insulin secreting cells.

18. A method according to claim 1, additionally comprising employing at least one second electrode for electrifying a second at least a part of an abdominal region, wherein said second electrode supplies a second AC pulse different from said AC pulse of said electrode.

19. A method according to claim 18, wherein said second pulse is designed to suppress insulin secretion.

20. A method according to claim 1, wherein said second pulse is designed to hyper-polarize said a second at least a part of an abdominal region.

21. A method according to claim 1, wherein said AC pulse is not applied at every action potential of said cell.

22. A method according to claim 1, wherein said AC pulse is not applied at every burst activity of said cell.

23. A method according to claim 1, wherein said AC pulse has a duration of less than a single action potential of said cell.

24. A method according to claim 23, wherein said AC pulse has a duration of less than a plateau duration of said cell.

25. A method according to claim 1, wherein said AC pulse has a duration of longer than a single action potential of said cell.

26. A method according to claim 1, wherein said AC pulse has a duration of longer than a burst activity duration of said cell.

27. A method according to claim 1, additionally comprising administering a pharmaceutical treatment to said body containing said pancreas.

28. A method according to claim 27, wherein said pharmaceutical treatment comprises a pancreatic treatment.

29. A method according to claim 27, wherein said AC pulse counteracts adverse effects of said pharmaceutical treatment.

30. A method according to claim 27, wherein said AC pulse synergistically interacts with said pharmaceutical treatment.

31. A method according to claim 27, wherein said AC pulse counteracts an adverse effect of pacing stimulation of said cell.

32. A method according to claim 1, wherein applying an AC pulse via said electrode to the abdominal region comprises applying a pulse of less than 2000 Hz.

33. A method according to claim 2, wherein applying an AC pulse via said electrode to the abdominal region comprises applying a pulse of less than 2000 Hz.

34. A method according to claim 1, wherein implanting an electrode comprises implanting an electrode and lead.

35. A method according to claim 2, wherein implanting an electrode comprises implanting an electrode and lead.

36. A method according to claim 1, wherein implanting an electrode comprises implanting an electrode intra-abdominally.

37. A method according to claim 2, wherein implanting an electrode comprises implanting an electrode intra-abdominally.

38. A method according to claim 1, wherein applying comprises intentionally stimulating tissue near said at least one electrode and to which said at least one electrode is not attached or in contact with, by said applying an AC pulse.

39. A method according to claim 2, wherein applying comprises intentionally stimulating tissue near said at least one electrode and to which said at least one electrode is not attached or in contact with.

40. A method according to claim 1, wherein applying comprises intentionally reducing said blood glucose level.

41. A method according to claim 2, wherein applying comprises intentionally reducing said blood glucose level.

42. A method according to claim 1, wherein said applying comprises applying said AC pulse to a plurality of spaced apart tissue regions, using a same electrode.

43. A method according to claim 2, wherein said applying comprises applying said AC pulse to a plurality of spaced apart tissue regions, using a same electrode.

44. A method according to claim 1, wherein said applying comprises applying different electrification to different spaced apart tissue regions, using a plurality of electrodes.

45. A method according to claim 2, wherein said applying comprises applying different electrification to different spaced apart tissue regions, using a plurality of electrodes.

46. A method according to claim 1, wherein said AC pulse includes a bi-phasic pulse of at least 10 ms in duration.

47. A method according to claim 2, wherein said AC pulse includes a bi-phasic pulse of at least 10 ms in duration.

* * * * *